(12) United States Patent
Hocking

(10) Patent No.: US 11,510,585 B2
(45) Date of Patent: Nov. 29, 2022

(54) METHOD TO QUANTIFY THE HEMODYNAMIC AND VASCULAR PROPERTIES IN VIVO FROM ARTERIAL WAVEFORM MEASUREMENTS

(71) Applicant: Grant Hocking, Alpharetta, GA (US)

(72) Inventor: Grant Hocking, Alpharetta, GA (US)

(*) Notice: Subject to any disclaimer, the term of this patent is extended or adjusted under 35 U.S.C. 154(b) by 503 days.

(21) Appl. No.: 16/744,707

(22) Filed: Jan. 16, 2020

(65) Prior Publication Data
US 2020/0229714 A1 Jul. 23, 2020

Related U.S. Application Data

(60) Provisional application No. 62/793,594, filed on Jan. 17, 2019.

(51) Int. Cl.
| | |
|---|---|
| *A61B 5/00* | (2006.01) |
| *A61B 5/026* | (2006.01) |
| *A61B 5/022* | (2006.01) |
| *A61B 5/0295* | (2006.01) |
| *A61B 5/0265* | (2006.01) |
| *A61B 5/0285* | (2006.01) |

(52) U.S. Cl.
CPC ............ *A61B 5/0261* (2013.01); *A61B 5/022* (2013.01); *A61B 5/0265* (2013.01); *A61B 5/0285* (2013.01); *A61B 5/0295* (2013.01); *A61B 5/681* (2013.01); *A61B 2562/0261* (2013.01)

(58) Field of Classification Search
CPC ..... A61B 5/0261; A61B 5/022; A61B 5/0265; A61B 5/0285; A61B 5/0295; A61B 5/681; A61B 2562/0261; A61B 5/02007; A61B 5/029; A61B 5/02108; A61B 5/02028
See application file for complete search history.

(56) References Cited

U.S. PATENT DOCUMENTS

| | | |
|---|---|---|
| 2002/0095087 A1 | 7/2002 | Mourad et al. |
| 2003/0135124 A1 | 7/2003 | Russell |
| 2008/0033305 A1 | 2/2008 | Hatib et al. |
| 2009/0270695 A1 | 10/2009 | McEowen |
| 2016/0302672 A1 | 10/2016 | Kuri |

OTHER PUBLICATIONS

The International Search Report/Written Opinion released in the corresponding International Application, PCT/US2020/013830, dated Apr. 6, 2020; 11 pages.

*Primary Examiner* — Joel Lamprecht
(74) *Attorney, Agent, or Firm* — Smith Gambrell & Russell LLP

(57) ABSTRACT

Disclosed herein are in vivo non-invasive methods and devices for the measurement of the hemodynamic parameters and aortic valve conformance and compliance in a subject. The method requires measuring the peripheral pulse volume waveform (PVW), the peripheral pulse pressure waveform (PPW), and the peripheral pulse velocity waveform (PUW) from the same artery using a non-invasive device. The waveforms PPW and PUW are used to calculate the waveform dPdU which is used to determine aortic valve ejection volume, closure volume, and quality factor, as well as stroke volume and cardiac output. The disclosed methods and devices are useful in the diagnosis and treatment of aortic valve disease, disorders, and dysfunction.

26 Claims, 12 Drawing Sheets

METHOD TO QUANTIFY THE HEMODYNAMIC AND VASCULAR PROPERTIES IN VIVO FROM ARTERIAL WAVEFORM MEASUREMENTS

CLAIM OF PRIORITY

This application claims priority from U.S. Provisional Patent Application Ser. No. 62793594, filed Jan. 17, 2019, which is incorporated herein in its entirety.

FIELD OF THE INVENTION

The present invention generally relates to the quantification of the hemodynamic parameters and hypertension status of a living subject. More specifically, the present invention relates to systems and methods of using sensed peripheral arterial pulse waveform measurements to assess hemodynamic parameters, such as hypertensive state, cardiac output, vasodilation or vasocontraction, and, also to quantify the mechanical anelastic properties of the blood vessels in vivo.

BACKGROUND OF THE INVENTION

Conventional methods of establishing the hypertensive state of a subject involves blood pressure measurements, and depending on the state of the subject's hypertension, medication may be prescribed to lower the subject's blood pressure. The effectiveness of such medication is monitored by blood pressure measurements. If the medication lowers the subject's blood pressure to acceptable levels, then it is presumed that the medication is considered effective in controlling the subject's hypertension. The impacts that the prescribed medication have on the subject in general, and in particular the subject's blood vessels are unknown.

In subjects experiencing angina pectoris, glyceryl trinitrate may be prescribed as a vasodilator to inhibit the onset of angina pectoris during exercise. The effectiveness of the medication on specific subjects is basically trial and error. During vasodilation, the blood vessels change their properties significantly. Without diagnostic measurements of these changes, the impact of the medication, and its potential impact on the subject's blood vessels is unknown. Angina can also be due to narrowed or blocked arteries around the heart, ischemia, emotional stress, exposure to very hot or cold temperatures, heavy meals and smoking.

The changes to the arterial vascular vessels mechanical properties from hypertension, aging, diabetes, mellitus, arteriosclerosis, hypercholesterolemia and ischemic heart disease are difficult to quantify with common procedures such as simple pulse wave velocity (PWV) measurements, electrocardiogram (EKG) and blood pressure measurements. The anelastic in vivo properties of the peripheral arterial blood vessels and their hypertrophy can provide valuable insight into the effect of these processes on a subject's wellbeing, and the impact of medication to treat such disorders and their associated changes to the subject's arterial vascular vessel properties. The acute effect of vasoconstriction and vasodilation with resulting increase and decrease in blood pressure, have significant impact on the anelastic response of the body's peripheral arterial vascular vessels. In vivo quantification of these anelastic changes are essential in diagnosing the issues relating to aging and disease, and the impact of medication on changes to the peripheral arterial blood vessels' anelastic properties and their hypertrophy.

Arteries stiffen progressively with age and disease, even in the earliest stages of arteriosclerosis, prior to any clinical manifestation and anatomical evidence of the disease. In vivo quantification of minor changes in the peripheral artery blood vessels properties would provide an extremely useful clinical tool for the assessment of cardiovascular risk, from arterial vessel stiffening, plaque buildup, arteriosclerosis and/or elevated risk of aneurysm or dissection. PWV and augmentation index are associated with cardiovascular burden, but do not have the sensitivity necessary to detect minor changes in the hemodynamic parameters, such as cardiac output and the mechanical properties of the peripheral arterial blood vessels nor their hypertrophy. Alternative methods for such an assessment are urgently needed.

Therefore, it is an object of the invention to provide non-invasive systems and methods for the measurement of hemodynamic parameters and aortic valve conformance and compliance.

SUMMARY OF THE INVENTION

The present invention is an in vivo non-invasive method and apparatus for the measurement of hemodynamic parameters, such as cardiac output, hypertensive state and aging status of a subject, and the aortic valve compliance and conformance. The method requires measuring the peripheral pulse volume waveform (PVW), using an infra-red emitter and sensor positioned over an artery, a force sensor positioned over the same artery measuring the peripheral pulse pressure waveform (PPW), an snotty speech d a velocity sensor positioned over the same artery measuring the peripheral pulse velocity waveform (PUW), with all sensors contained in a wristband, that applies a slight force and being of adequate compliance, for the force sensor to measure the arterial pulse pressure waveform (PPW) as a tonometer. The waveforms PPW and PUW are used to calculate the dPdU waveform which is used to determine aortic valve ejection volume, closure volume, and Quality factor, as well as stroke volume and cardiac output.

When the device is placed over a subject's carotid artery, the stroke volume, cardiac output, aortic valve conformance and compliance, and the aorta PWV and Quality factor can be quantified. Rapid changes in stroke volume can warn of low blood volume, hypotension perfusion and the imminent risk of the subject entering shock conditions. From known values of the subject's systolic and diastolic blood pressure, the full mechanical anelastic properties of the peripheral arterial blood vessels in vivo can be determined, such as the pulse shear strain at systolic, the shear modulus, and the anelastic power law constants, during both the systolic and diastolic phases experienced by the arterial blood vessels over a cardiac cycle. From the time location of the second forward pulse wave in the PVW, the form of the hypertension of the subject can be quantified.

The change in the peripheral arterial blood vessels anelastic properties during vasodilation or vasocontraction, either from induced hypertension, physical exercise, breathing exercises or induced by medication, are quantified from the measured waveforms PVW and PPW. These changes in the arterial blood vessel anelastic properties, quantify the extent of vasodilation, vasocontraction or induced hypertension, and provide a direct measure of whether such vasodilation is sufficient in improving the tone of the subject's peripheral artery blood vessels, and thus reverse or slow the rate of change of the subject's hypertensive state. Historical recoding of a subject's vasodilation/vasocontraction on arterial blood vessel anelastic properties, enable physicians and caretakers to more accurately determine the impact of any prescribed medication, diet or exercise program on the subject's hypertensive state.

Other objects, features and advantages of the present invention will become apparent upon reviewing the following description of the preferred embodiments of the invention, when taken in conjunction with the drawings and the claims.

1C shows the back of the device 3 with a reflective pulse optical plethysmograph, force and velocity sensors 5 for positioning over the subject's radial artery, with all the sensors connected to the device 3.

Figure 2:
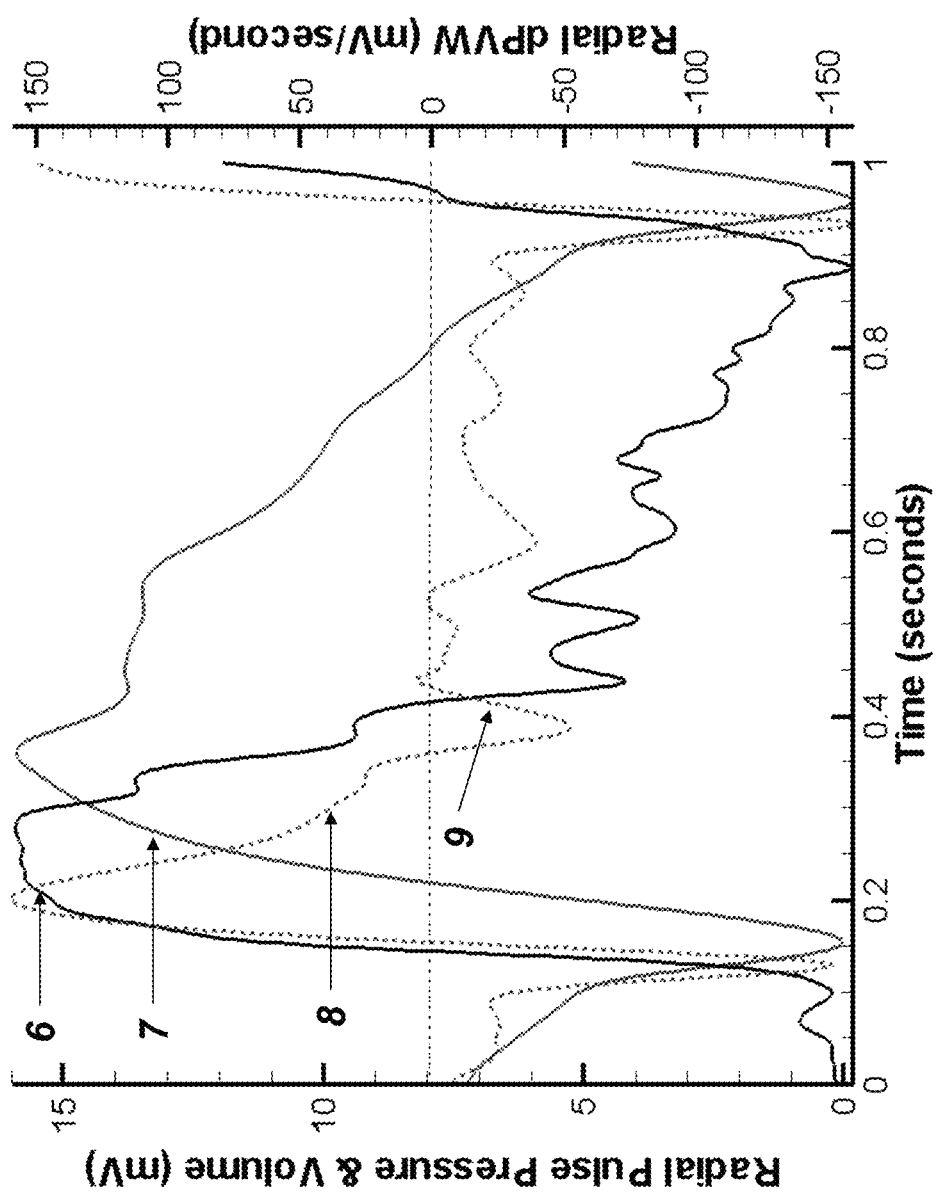

FIG. 2 is the time history of the peripheral pulse volume and pulse pressure waveforms, PVW and PPW, recorded from an optical plethysmograph and force sensor positioned over the radial artery, showing the out of phase of the two waveforms, due to the anelasticity of the artery blood vessels, and the time history of the constructed first time derivative of the PVW.

Figure 3:
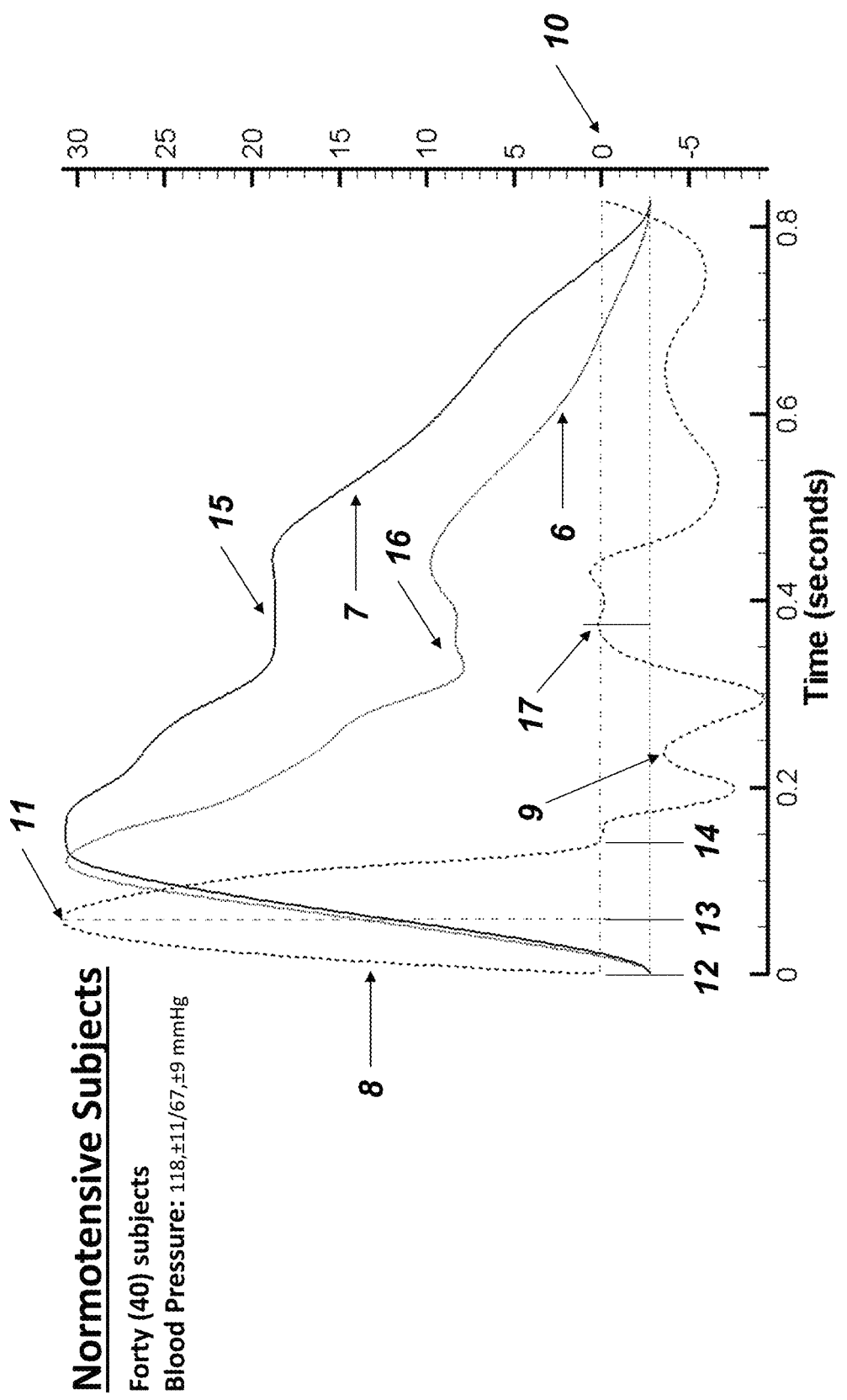

FIG. 3 is the averaged time history for the peripheral pulse optical plethysmograph waveform (PVW) of forty (40) normotensive (NT) subjects recorded from an optical plethysmograph sensor positioned over a finger, and the time history of the constructed first time derivative of the PVW, and the averaged time history of the peripheral arterial pulse pressure waveform (PPW) recorded over the radial artery.

Figure 4:
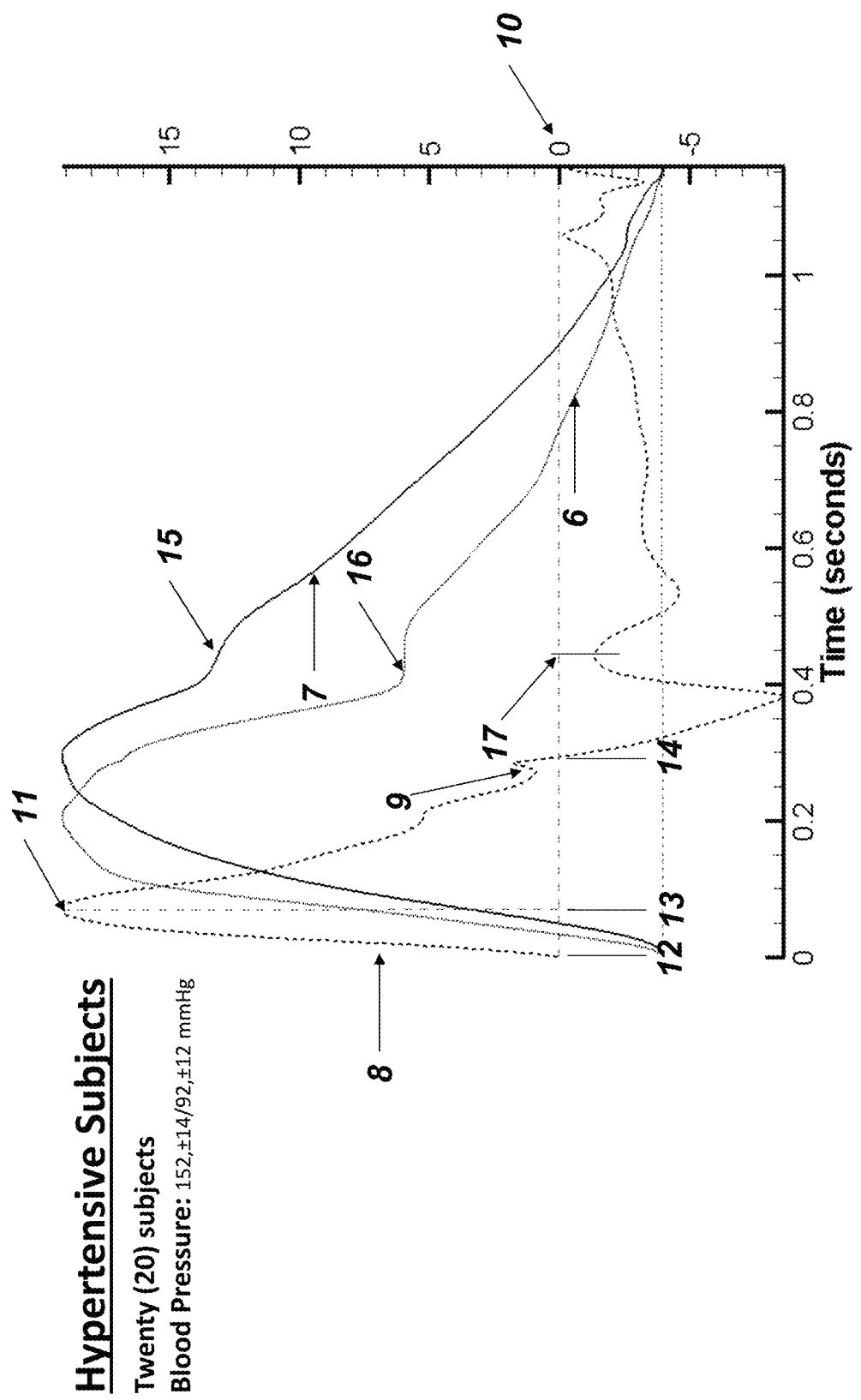

FIG. 4 is the averaged time history of the peripheral pulse optical plethysmograph waveform (PVW) for twenty (20) hypertensive (HT) subjects recorded from an optical plethysmograph sensor positioned over a finger, and the time history of the constructed first time derivative of the PVW, and the averaged time history of the peripheral arterial pulse pressure waveform (PPW) recorded over the radial artery.

Figure 5:
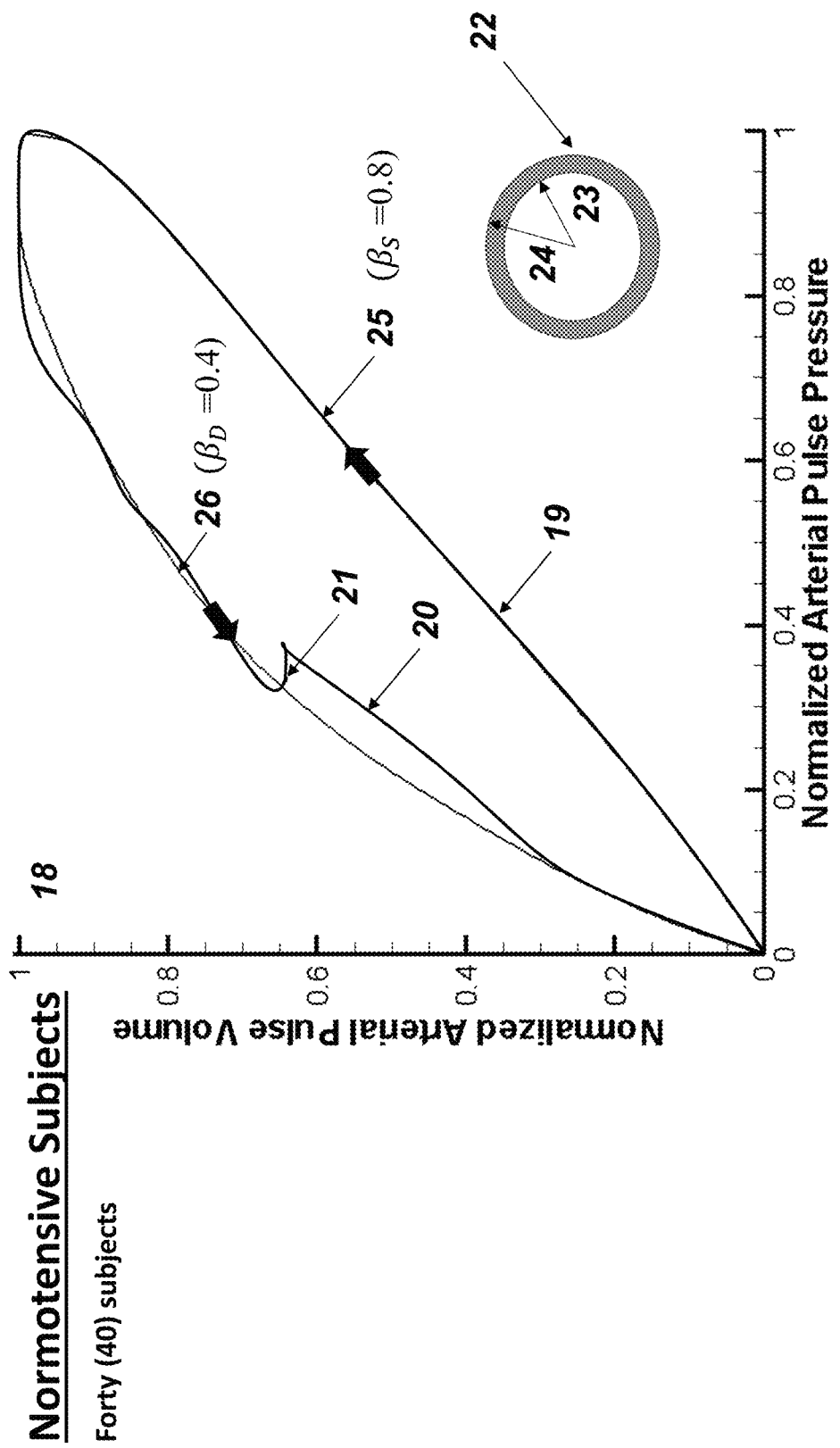

FIG. 5 is the normalized time shifted arterial pulse pressure plotted against the normalized arterial pulse volume as an average for forty (40) normotensive subjects, and the thick wall three (3) component anelastic power law model.

Figure 6:
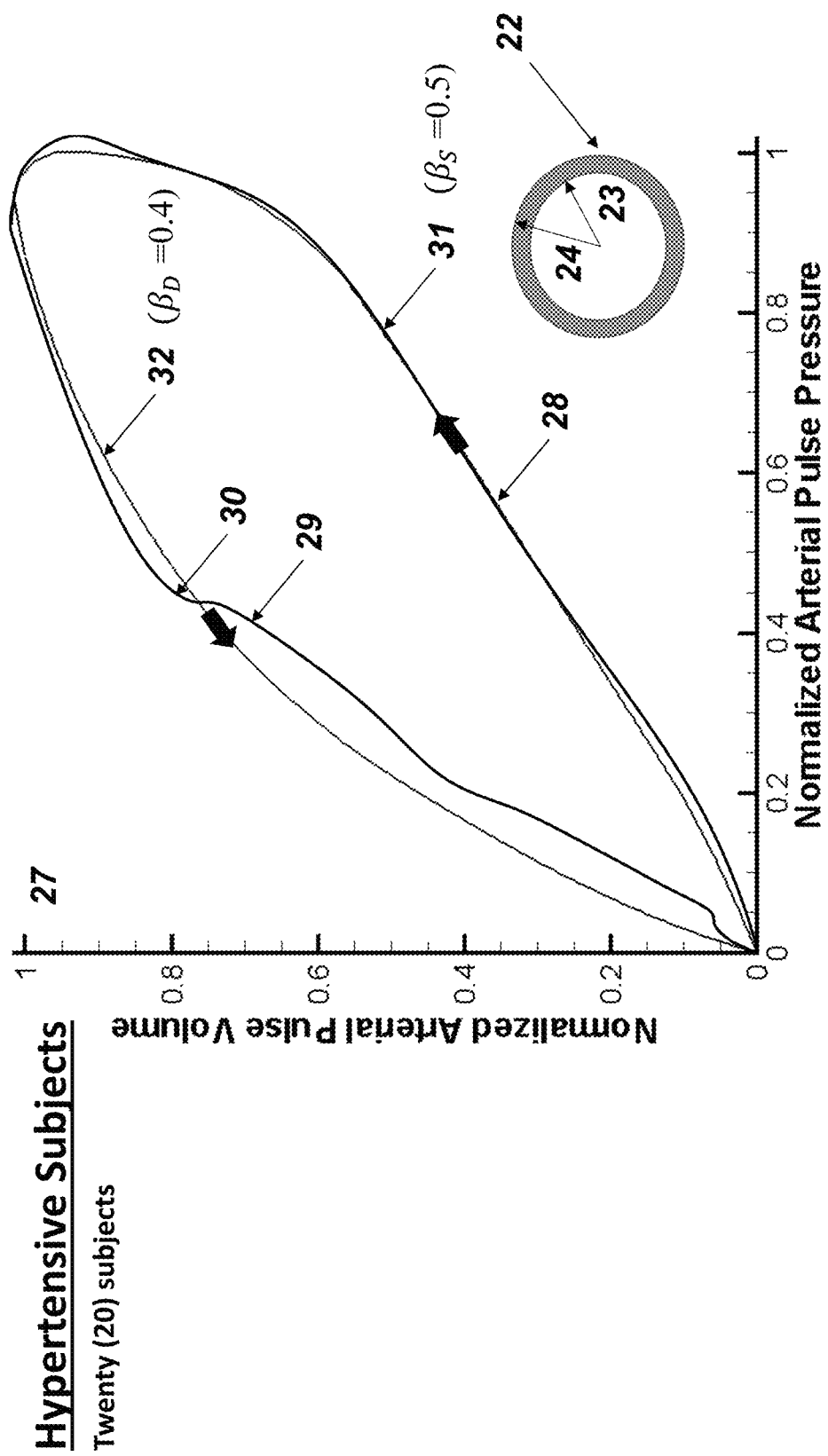

FIG. 6 is the normalized time shifted arterial pulse pressure plotted against the normalized arterial pulse volume as an average for twenty (20) hypertensive subjects, and the thick wall three (3) component anelastic power law model.

Figure 7:
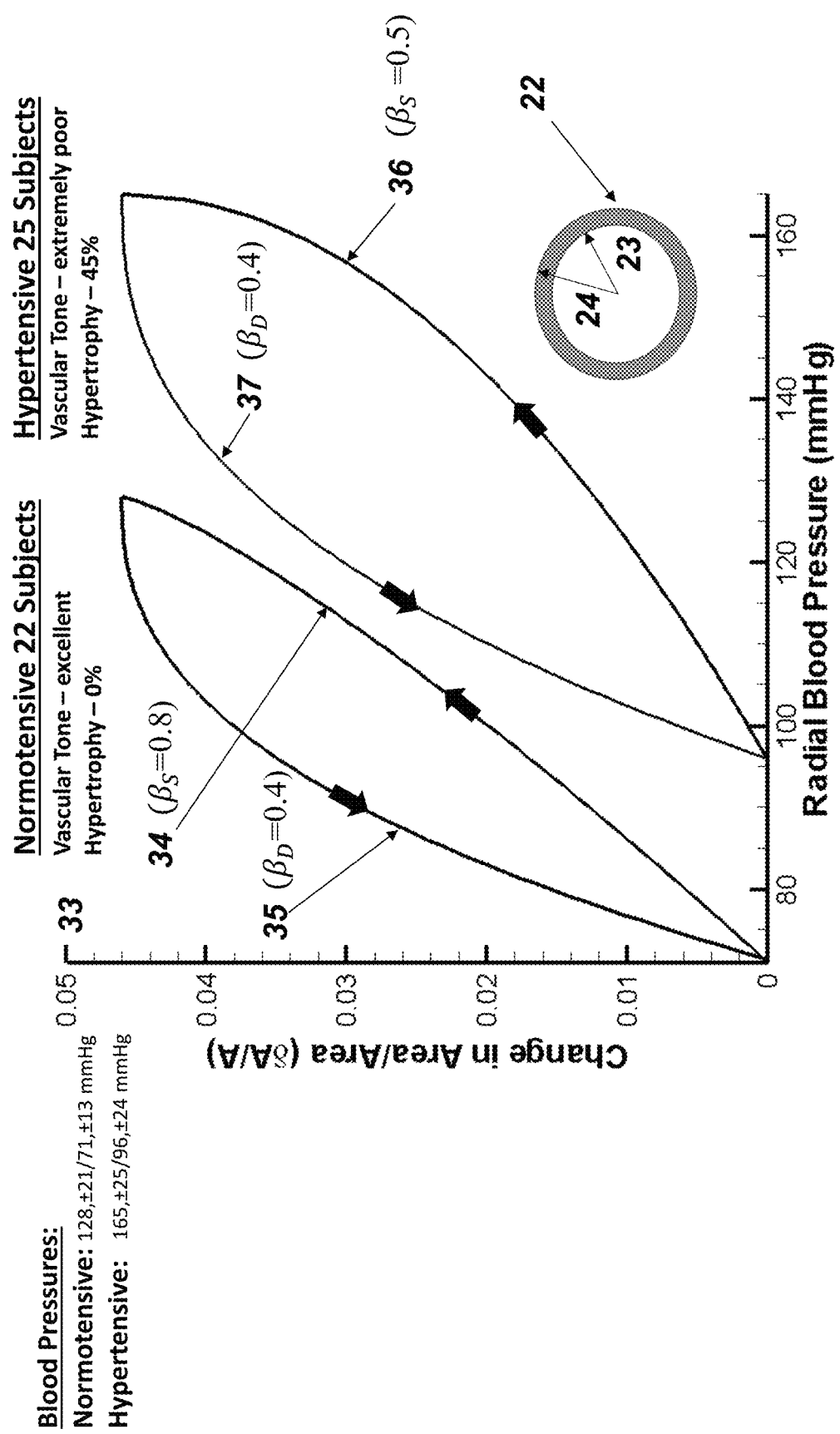

FIG. 7 is the time shifted arterial pulse pressure plotted against the arterial pulse volume as an average for twenty two (22) normotensive and twenty five (25) hypertensive subjects experiencing significant hypertrophy, and the thick wall three (3) component anelastic power law model.

Figure 8:
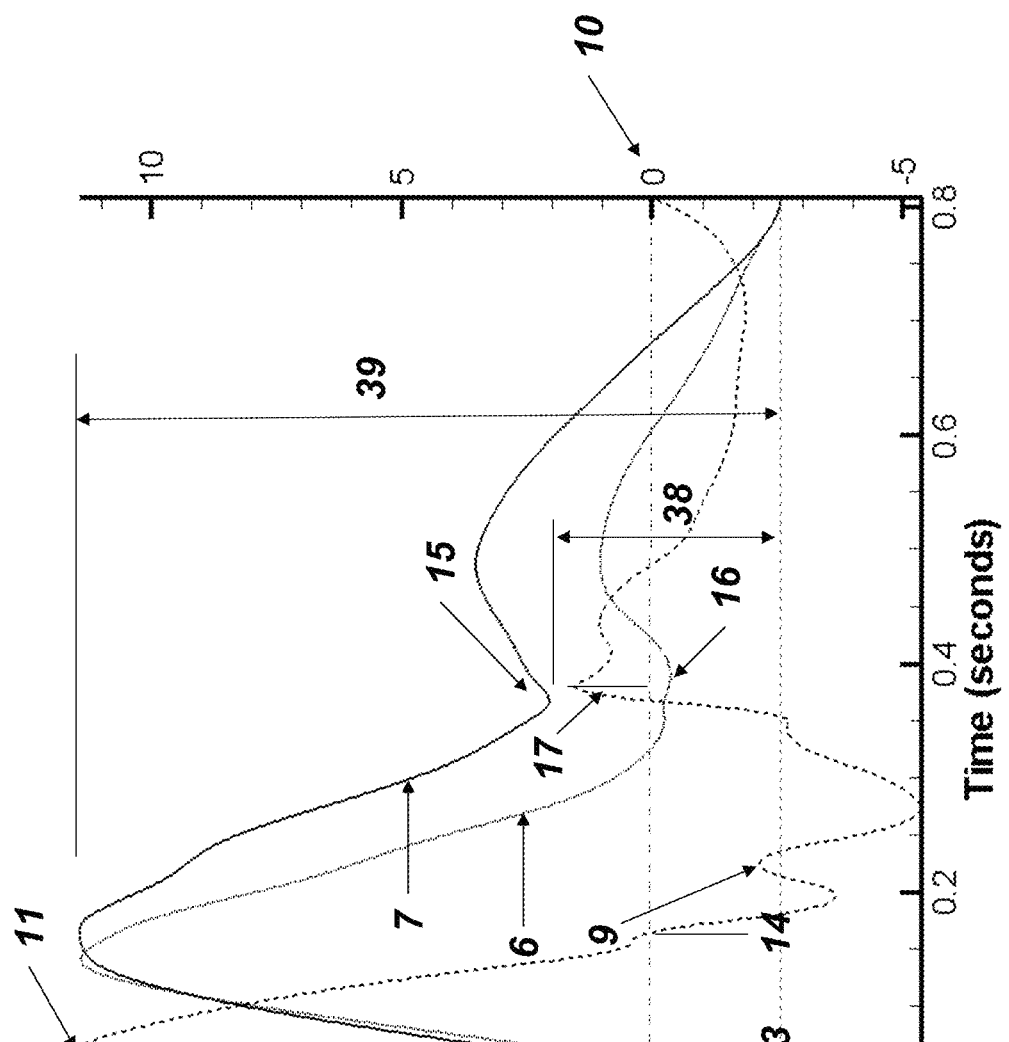

FIG. 8 is the averaged normalized time history of the peripheral pulse optical plethysmograph waveform (PVW) for a subset of twenty (20) of the forty (40) normotensive subjects following sublingual administration of 500 µg of glyceryl trinitrate (NTG), recorded from an optical plethysmograph sensor positioned over a finger, and the time history of the constructed first time derivative of the PVW, and the averaged time history of the peripheral arterial pulse pressure waveform (PPW) recorded over the radial artery.

Figure 9:
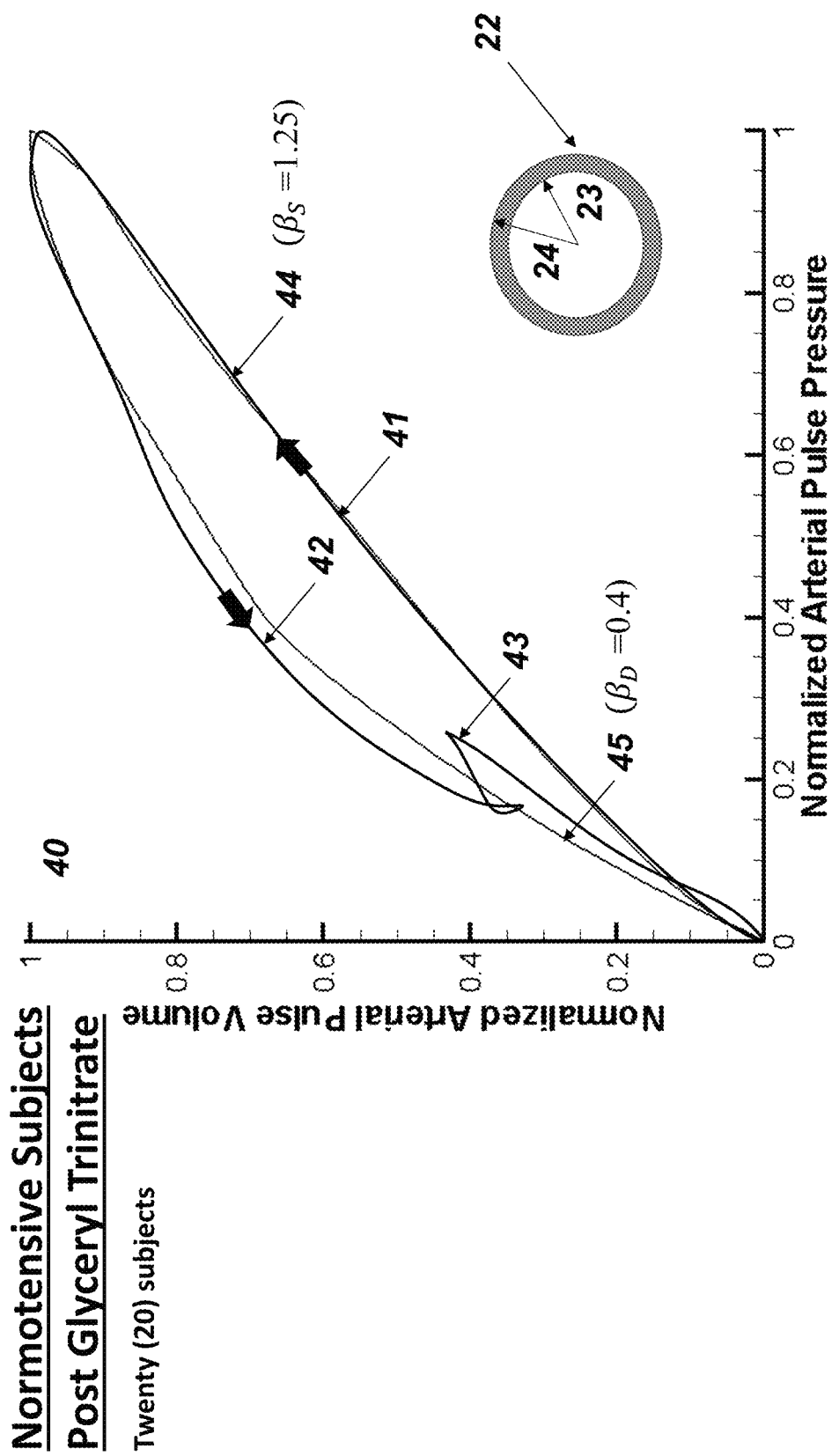

FIG. 9 is the normalized time shifted arterial pulse pressure plotted against the normalized arterial pulse volume as an average for the subset of twenty (20) normotensive subjects, three (3) minutes after sublingual administration of 500 µg of glyceryl trinitrate (NTG), and the thick wall three (3) component anelastic power law model.

Figure 10:
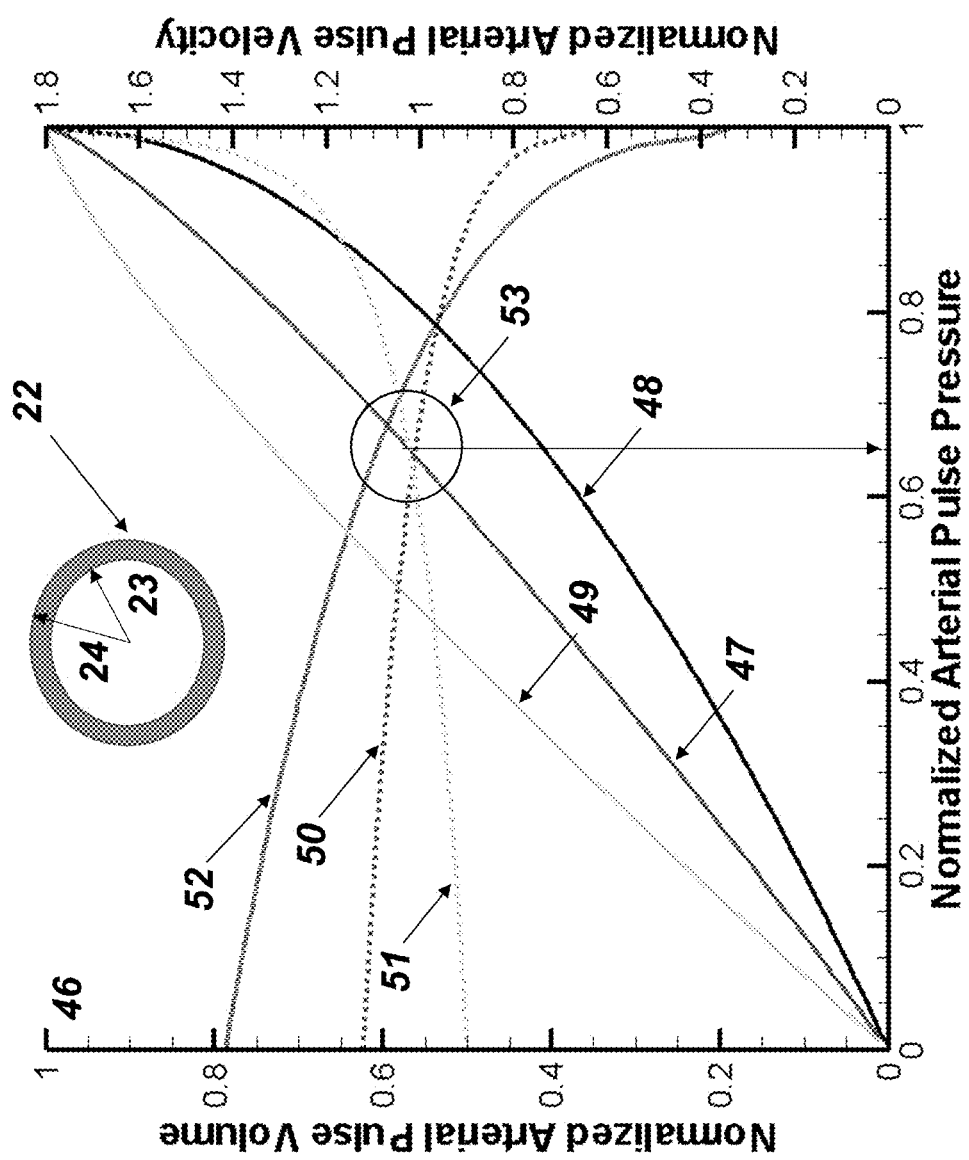

FIG. 10 is the normalized time shifted arterial pulse pressure plotted against the normalized arterial pulse volume and the normalized arterial pulse wave velocity for the pressurizing phase of the arteries, as an average of the forty (40) normotensive subjects, of the twenty (20) hypertensive subjects, and of the subset of twenty (20) normotensive subjects three (3) minutes after sublingual administration of 500 µg of glyceryl trinitrate (NTG), and the thick wall three (3) component anelastic power law model.

Figure 11:
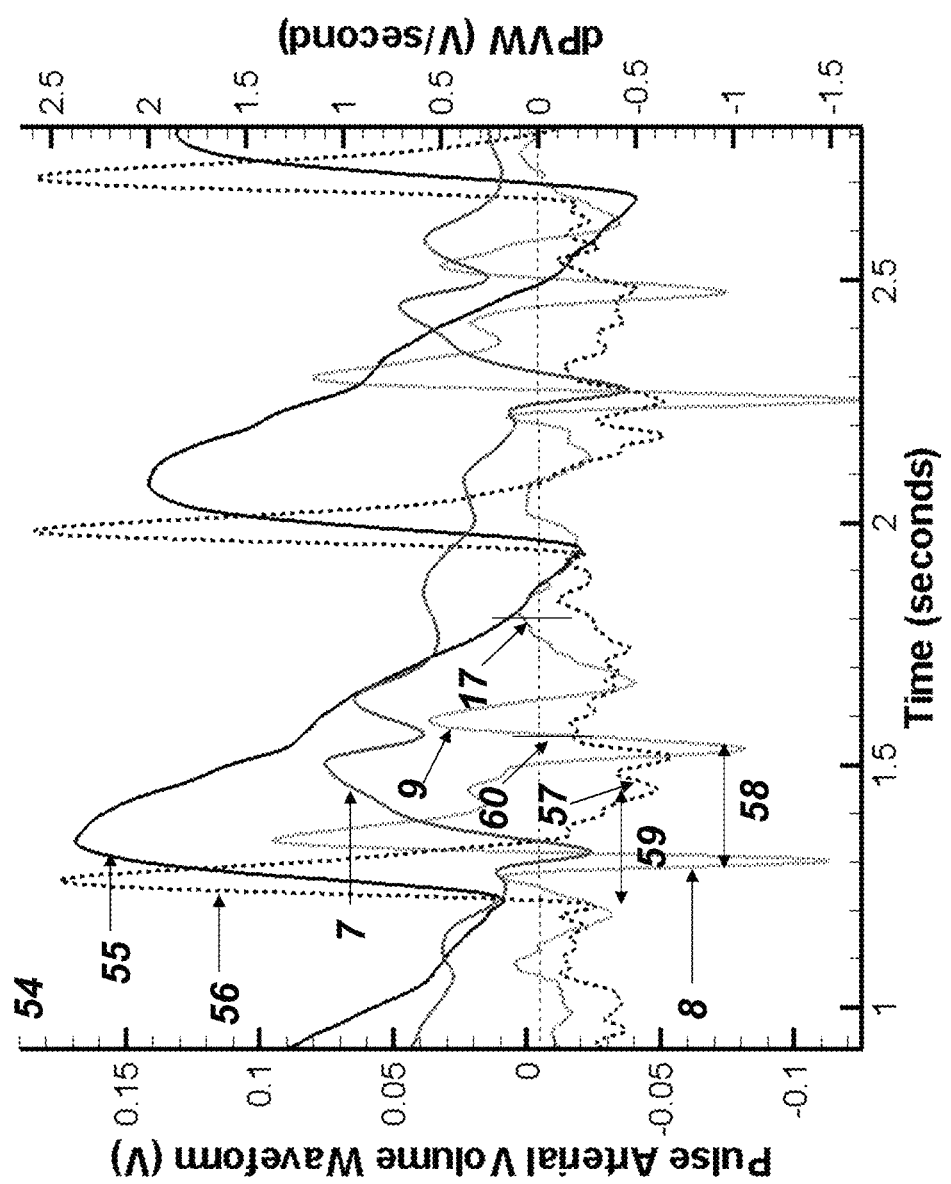

FIG. 11 is the time history of the peripheral pulse volume waveforms (PVW), before and after exercise, recorded from an optical plethysmograph sensor positioned over the radial artery, and the time history of the constructed first time derivative of the PVWs.

Figure 12B:
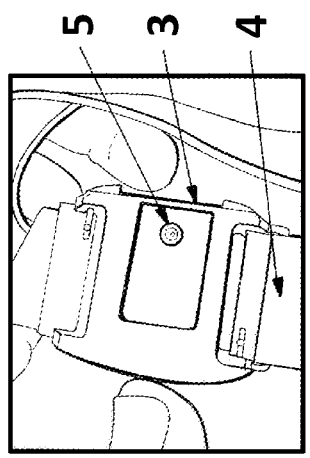
Figure 12C:
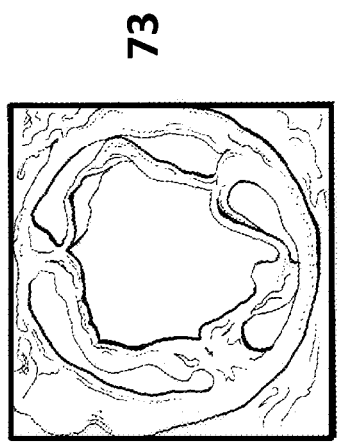
Figure 12D:
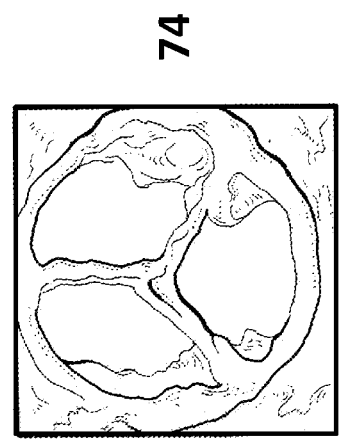
Figure 12A:
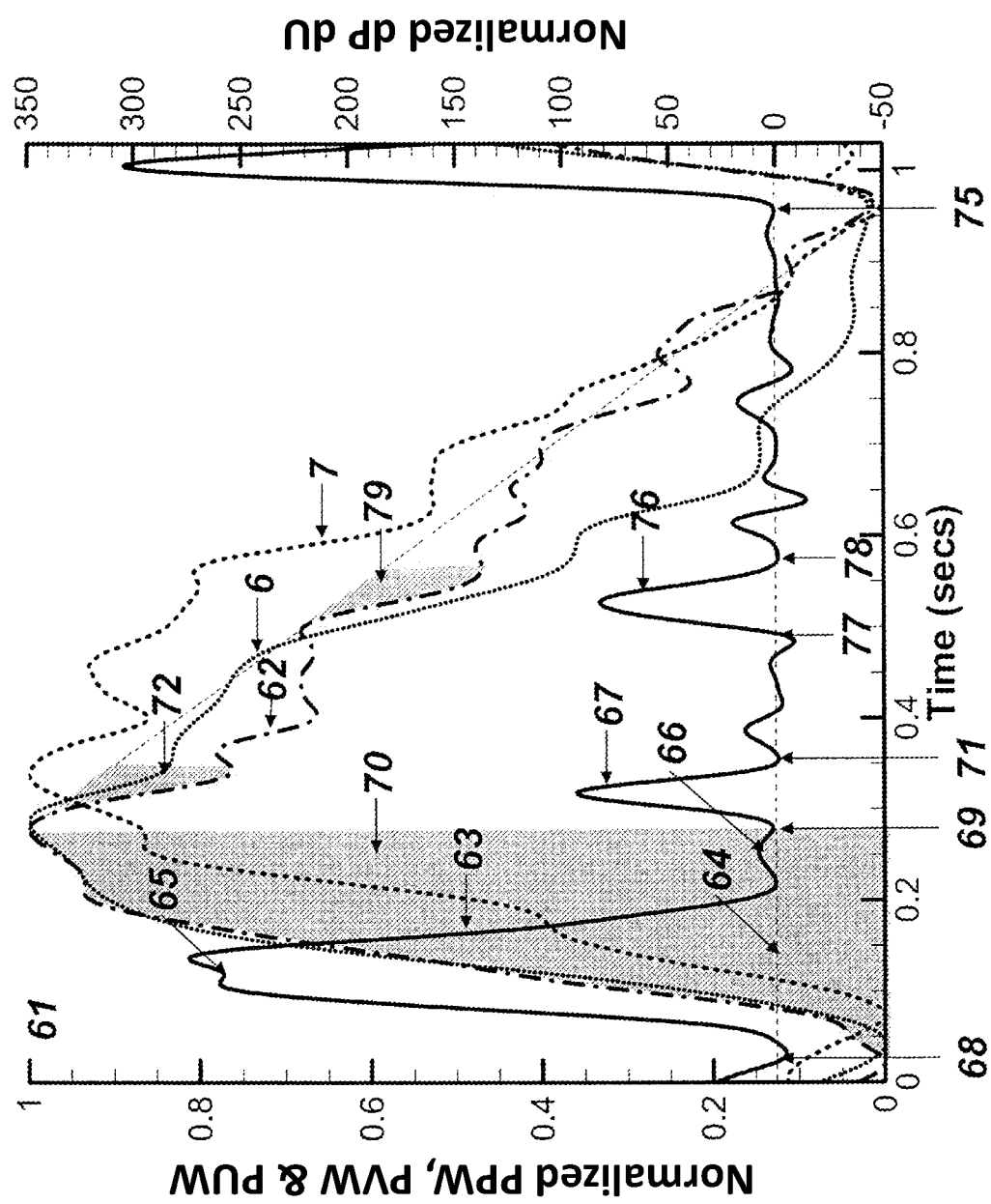

FIG. 12A is the time history of the peripheral pulse pressure (PPW), volume (PVW) and velocity waveforms (PUW), recorded from an optical plethysmograph, the force and velocity sensors positioned over the carotid artery, and the calculated wave intensity analysis (dPdU) waveform constructed from the waveforms PPW and PUW.

FIG. 12B shows a processing device 3 held in place by a strap 4, containing a reflective pulse optical plethysmograph, force and velocity sensors and pressure actuator 5 for positioning over the subject's radial artery, with all sensors and the pressure actuator connected to the device 3.

FIG. 12C shows the aortic valve in an open position.

FIG. 12D shows the aortic valve in a closed position.

DETAILED DESCRIPTION OF THE DISCLOSED EMBODIMENT

Disclosed herein is an in vivo non-invasive method and apparatus for the measurement of the hemodynamic parameters, such as cardiac output, hypertensive, hypertrophy and aging state of a subject, and the aortic valve conformation and compliance. The method requires non-invasively measuring the peripheral pulse volume waveform (PVW), the peripheral pulse pressure waveform (PPW), and the peripheral pulse velocity waveform (PUW) and using the measurements to determine hemodynamic properties and aortic valve conformation and compliance.

Figure 1A:
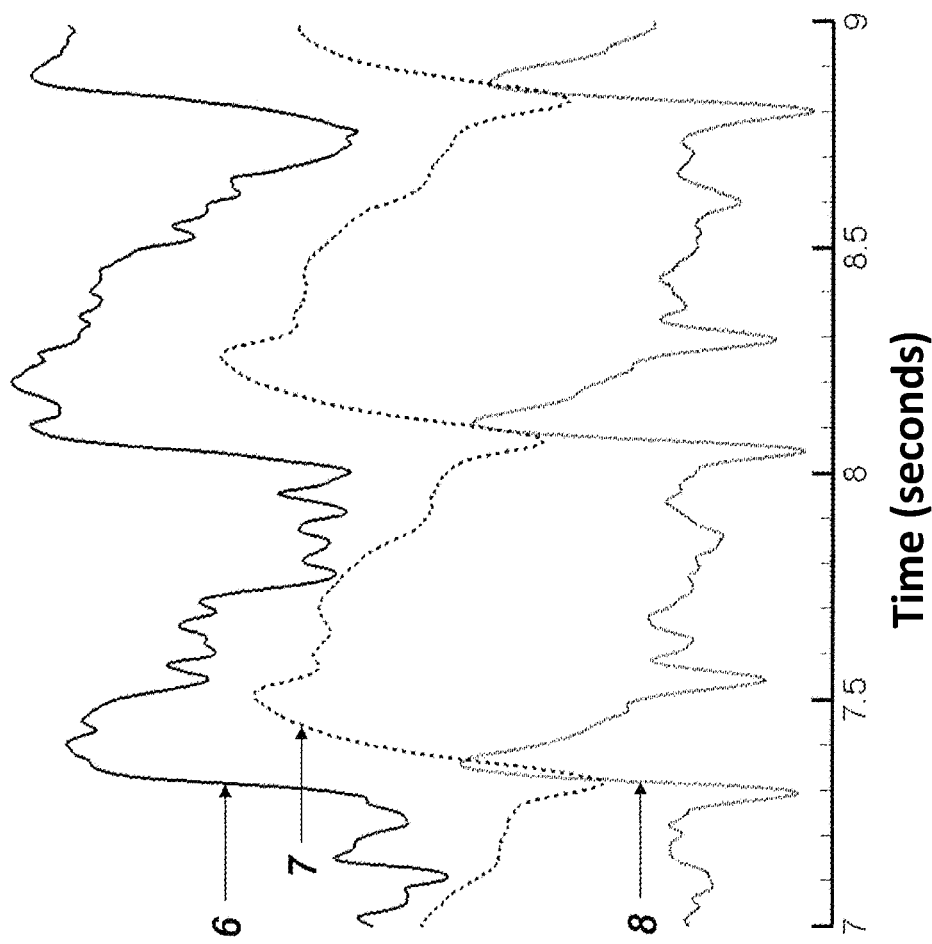
FIG. 1A is an exemplary plot that can be obtained using processing device 3. Waveform 6 is the peripheral arterial pulse pressure waveform (PPW), waveform 7 is the arterial pulse volume waveform (PVW), and waveform 8 is the first derivative of PVW.
Figure 1B:
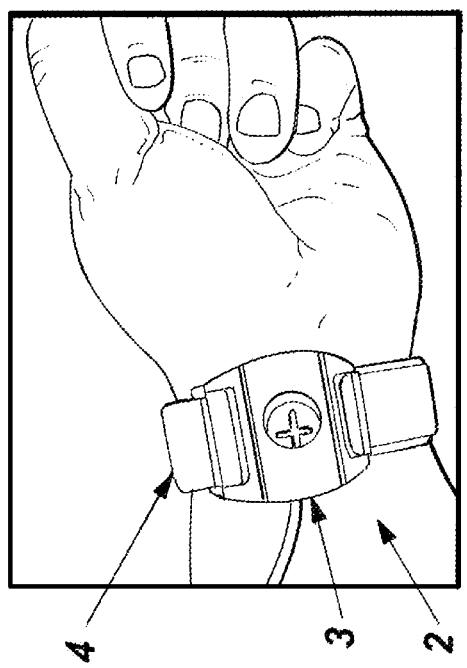
FIG. 1B is a view of an arm 2 of a subject with a processing device 3 held in place by strap 4. FIG.
Figure 1C:
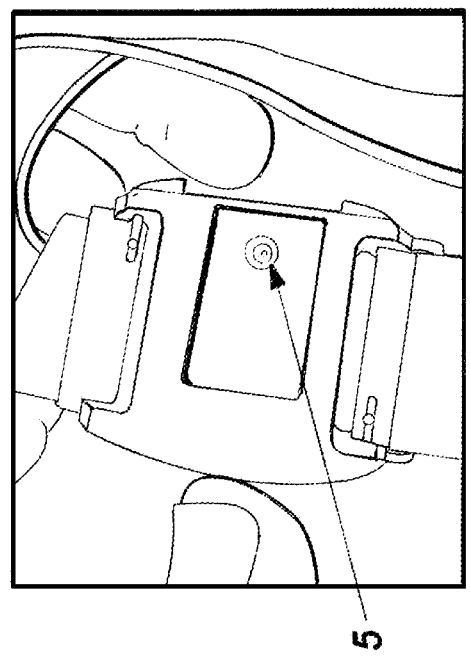

FIG. 1A shows the arm of the subject 2 with a processing device 3 held in place by a strap 4. Processing device 3 contains a sensor suite 5 which can include any variation of the following sensors: a reflective pulse optical plethysmograph, force sensors, and velocity sensors. The sensors can be connected to the device 3, or can be contained within the device 3.

The device can be designed to be positioned over an arterial vessel in a subject. In one embodiment, the arterial vessel can be the radial artery, brachial artery, axillary artery, carotid artery, femoral artery, or tibial artery. In a preferred embodiment, the device is designed as a neck strap to be positioned over the carotid artery.

Plethysmography is a method that is used to estimate the skin blood flow using infrared light. Traditionally, it is used to measure oxygen saturation, blood pressure, and cardiac output. Optical plethysmographs use an infrared light sent into the tissue and the amount of backscattered light corresponds with the variation of the blood volume. In one embodiment, the pulse optical plethysmograph sensor within the disclosed device is an infrared optical plethysmograph sensor, a visible light plethysmograph sensor, or a pulse oximetry sensor.

The force sensor could be of either a resistive, strain gage, piezoelectric, capacitance or mems type. The velocity sensor could be either a Hall sensor with an applied magnetic field either from a permanent magnet or an electrical activated electromagnet, or an ultrasound doppler velocity sensor to measure the arterial pulse velocity waveform (PUW).

The disclosed processing device 3 can also contain a motion sensor in the sensor suite 5. In such an embodiment, the motion sensor acts to ensure accurate results by only collecting and processing the waveforms PPW, PVW and PUW when the motion sensor is within certain threshold limits. The motion sensor can be either of the piezoelectric, accelerometer or mems type.

Methods of using the disclosed processing device to measure the hemodynamic parameters, such as cardiac output, hypertensive, hypertrophy and aging state of a subject, and the aortic valve compliance and conformance are disclosed. The current disclosure herein further improves upon previously disclosed methods by obtaining non-invasive measurements of the peripheral pulse volume waveform (PVW), the peripheral pulse pressure waveform (PPW), and the peripheral pulse velocity waveform (PUW) and using the measurements to determine hemodynamic parameters and mechanistic anelastic properties of arterial blood vessels in a subject. The hemodynamic parameters and mechanistic anelastic properties can then be used to diagnose disease, determine the efficacy of drug treatments, monitor patients having pneumonia, cardiac disorders, sepsis, asthma, obstructive sleep apnea, hypopnea, anesthesia, pain, or narcotic use, or other means in which close, real time monitoring of cardiac function are necessary.

In one embodiment, the peripheral pulse volume (PVW) measurement is obtained using an infra-red emitter and sensor positioned over an artery. The peripheral pressure waveform (PPW) is obtained by a force sensor positioned over the same artery. The peripheral pulse velocity waveform (PUW) is obtained by a velocity sensor placed over the same artery. All of the aforementioned sensors are contained in the disclosed wristband device that applies an appropriate amount of force such that the device acts as a tonometer.

The waveforms, PPW, PVW and PUW, can be transformed by either Fast Fourier Transform FFT or the power spectral density method to determine the respiratory and heart rates and associated higher frequencies. The time phase shift between the PPW and PVW, and the plot of pulse pressure versus pulse volume, quantifies the anelastic properties of the peripheral arterial blood vessels in vivo.

In one embodiment, the device is placed over a subject's carotid artery, to quantify the stroke volume, cardiac output, aortic valve conformance and compliance, and the aorta PWV and Quality factor. From known values of the subject's systolic and diastolic blood pressure, the full mechanical anelastic properties of the peripheral arterial blood vessels in vivo can be determined, such as the pulse shear strain at systolic, the shear modulus, and the anelastic power law constants, during both the pressurizing and depressurizing phases experienced by the arterial blood vessels. From the time location of the second forward pulse wave in the PVW, the form of the hypertension of the subject can be determined.

The change in the peripheral arterial blood vessels anelastic properties during vasodilation or vasocontraction, either from induced hypertension, physical exercise, breathing exercises or induced by medication, are quantified from the measured waveforms PVW and PPW. These changes in the arterial blood vessel anelastic properties, quantify the extent of vasodilation, vasocontraction or induced hypertension, and provide a direct measure of whether such vasodilation is sufficient in improving the tone of the subject's peripheral artery blood vessels, and thus reverse or slow the rate of change of the subject's hypertensive state. Historical recoding of a subject's vasodilation/vasocontraction on arterial blood vessel anelastic properties enable physicians and caretakers to more accurately determine the impact of any prescribed medication, diet or exercise program of the subject's hypertensive state.

FIG. 2 shows the two measured waveforms, the PPW 6, the PVW 7 and its first time derivative dPVW 8, with the prime reflected forward wave shown as 9 on the waveform dPVW. The measurements were obtained using the wristband device disclosed herein. The applied pressure of the housing over the artery is greater than 10 mmHg and less than 50 mmHg. A motion sensor was contained in 5, and the waveforms PPW, PVW and PUW were only collected and processed when the motion sensor was within certain threshold limits.

FIG. 3 shows the peripheral arterial pulse optical plethysmograph waveform (PVW) for the averaged normalized one heart cycle time history for forty (40) normotensive subjects, denoted as 7, recorded from an optical plethysmograph sensor positioned over a finger. Also shown is the time history of the constructed first time derivative of the PVW being the dPVW, denoted as 8, with the prime reflected forward wave shown as 9 on the waveform dPVW, and the averaged normalized time history of the peripheral arterial pulse pressure waveform (PPW) recorded over the radial artery by applanation tonometry by a piezo-resistive cantilever transducer. The PPW was time shifted to be in-phase with the PVW, as denoted by 6. The measured waveforms, Millasseau et al., 2000, were normalized prior to being averaged for the forty (40) healthy normotensive subjects, aged from 24 to 80 years. All forty of the subjects had no previous history of hypertension or cardiovascular disease, and all were normotensive (office blood pressure <140/90 mm Hg), prior to the time of the study. Blood pressure measurements during the study were (mean, ±standard deviation) 118, ±11/67, ±9 mm Hg. The zero ordinate of the dPVW constructed waveform is shown as 10. The first pulse wave peak is denoted as 11. The rise and fall time intervals of the first pulse wave are given by the difference in the time abscissa of points denoted as 12, 13 and 14. With the points, being the intersection of the zero ordinate 10 and the constructed waveform dPVW, point 12 being the start of the rise of the first pulse wave, point 13 being the maximum of the first pulse wave, and point 14 being the end of the fall of the first pulse wave.

The ratio of the fall time to the rise time of the first pulse wave for the normotensive subjects as determined from points 12, 13 and 14 is 1.8. The rise and fall times of the first and subsequent pulse waves are important and highly dependent on the peripheral arterial blood vessel mechanical anelastic properties. The pulse is a soliton and as such maintains its shape virtually unattenuated provided the energy lost by anelasticity is equivalent to the loss due to dispersion. When these losses are equal, the pulse wave travels as a soliton with no change in shape until it interacts with another forward or backward traveling pulse wave, and upon separation of the two interacting soliton waves, the waves have the same shape to that before the interaction, and there is only a time shift to distinguish that the two waves have undergone an interaction. The solution of the interaction of two solitons is not linear, and so requires a non-linear approach to differentiation between the various pulse waveform. If the energy lost by anelasticity of the peripheral blood vessels deviates from a Quality factor (defined later in equation (2)) of Q=3, then the shape (fall and rise times) of the first pulse wave will change, and it is this change that can be directly correlated to the peripheral arterial blood vessel anelastic properties. The second forward pulse wave is shown as 15 on the pulse volume waveform PVW, 7, and is also shown as 16 on the measured pulse pressure waveform, 6. The second forward pulse wave, which causes closure of the aortic valve, is shown as 17 on the waveform dPVW, and its peak arrival time position in the heat beat cycle is 0.37 seconds.

FIG. 4 shows the peripheral pulse optical plethysmograph waveform (PVW), denoted as 7, for averaged normalized one heart cycle time history for twenty (20) hypertensive subjects, recorded from an optical plethysmograph sensor positioned over a finger. Also shown is the time history of the constructed first time derivative of the PVW being the dPVW, denoted as 8, with the prime reflected forward wave shown as 9 on the waveform dPVW, and the averaged normalized time history of the peripheral arterial pulse pressure waveform (PPW) recorded over the radial artery by applanation tonometry by a piezo-resistive cantilever transducer, and time shifted to be in-phase with the PVW, as denoted by 6. The averaged normalized time history of the peripheral arterial pulse pressure waveform recorded over the radial artery by applanation tonometry by a piezo-resistive cantilever transducer (PAP), is denoted as 9. The measured waveforms, Millasseau et al., 2000, were normalized prior to being averaged for the twenty (20) hypertensive subjects, aged from 24 to 80 years. Hypertension was diagnosed on the basis of >3 measurements of office blood pressure >140/90 mm Hg, with each measurement separated by at least a week. None of the hypertensive subjects had clinical evidence of cardiovascular disease other than hypertension. Twelve (12) of the subjects were receiving antihypertensive therapy at the time of the study, (diuretics, 7 of 12; β-adrenoreceptor antagonists, 5 of 12; a-adrenoreceptor antagonists, 1 of 12; ACE inhibitors, 3 of 12; angiotensin II receptor antagonists, 2 of 12; and calcium channel blockers, 4 of 12). Blood pressure at the time of the study for the hypertensive subjects was 152, ±14/92 ±12 mm Hg. The zero ordinate of the constructed waveform dPVW is shown as 10. The first pulse wave peak is denoted as 11.

The rise and fall time intervals of the first pulse wave are given by the difference in the time abscissa of points denoted as 12, 13 and 14. With the points, being the intersection of the zero ordinate 10 and the constructed waveform dPVW, point 12 being the start of the rise of the first pulse wave, point 13 being the maximum of the first pulse wave, and point 14 being the end of the fall of the first pulse wave.

The ratio of the fall time to the rise time of the first pulse wave for the normotensive subjects as determined from points 12, 13 and 14 is 3.4, a significant difference from the ratio determined for the normotensive subjects, which was 1.8. Normalizing the fall to rise time ratio to the normotensive subjects, the normalized fall to rise time for the hypertensive subjects is 1.9, and by construction of a Hypertensive Index (HI) from the forty (40) normotensive subjects as a HI=0, and the twenty (20) hypertensive subjects having a HI=100. Determining the fall to rise time ratio from the constructed waveform dPVW for any subject, the Hypertensive Index (HI) of that subject can be determined and its value will be equal to 0 for healthy normotensive subjects, but generally range from 0 to 100 for most subjects, and in cases of extreme hypertension can be >100. In some cases, the Hypertensive Index (HI) could be <0, for healthy subjects under extreme conditions such as exposure to temperature, altitude, and dehydration. The Hypertensive Index (HI) of a subject can be correlated to age, and as such can determine whether elevated levels of the Hypertensive Index (HI) are related to the effects of aging, or being accelerated due to the impacts of disease, life style or medication on the respective subject.

The second forward pulse wave is shown as 15 on the pulse volume waveform PVW, 7, and is also shown as 16 on the measured pulse pressure waveform, 6. 1 The second forward pulse wave, which causes closure of the aortic valve, is shown as 17 on the dPVW waveform, and its peak arrival time position in the heat beat cycle is 0.45 seconds. The peak time arrival of the second forward pulse wave was 0.37 seconds for the normotensive subjects, whilst the peak time arrival for the hypersensitive subjects was 0.45 seconds. The normalized time arrival of the second forward pulse wave from the normotensive subjects to the hypertensive subjects is attributed solely to being genetically positive to hypertension, and not considered to be age related hypertension.

Alternatively, a piezoelectric sensor placed over the artery can better detect both the time location of the second forward pulse wave, and by integrating the piezoelectric sensor in the vicinity of the second forward pulse wave time location, the pulse volume change can be better determined for aged subjects or subjects suffering from arteriosclerosis, hypertension or severe skin decolorization. The rate of pulse volume change in the vicinity of the second forward pulse wave can be determine over time and raise alerts if this time rate of change of pulse volume starts to accelerate.

FIG. 5 shows the normalized arterial pulse pressure versus normalized arterial pulse volume, denoted as 18, for the forty (40) normotensive subjects constructed from the time shifted waveform PPW and the waveform PVW, denoted earlier as 6 and 7 respectively. The rise (pressurizing) portion of the pulse pressure versus pulse volume is shown as 19, and the fall (depressurizing) portion is denoted as 20. Note that the fall portion 20 of the plot experiences load/unload cycles as denoted by 21.

FIG. 5 shows the three (3) component thick wall anelastic power law model denoted as 22, with inner wall radius 23 and outer wall radius 24, fitted to the normalized arterial pulse pressure versus normalized arterial pulse volume for the forty (40) normotensive subjects.

$$\left(\frac{\delta A}{A}\right) = \left(\frac{\beta_S \Delta P}{G_R\left(1-\left(\frac{a}{b}\right)^{2\beta_S}\right)}\right)\left[1-\left(\frac{\Delta P-P}{\Delta P}\right)^{\beta_S}\right] \quad (1)$$

The anelastic power law model is an analytical closed form solution of an incompressible material described by equation (1) for the systolic, pressurizing (loading) path, with a similar equation for the diastolic, depressurizing (unloading) path. The anelastic model has a power law coefficient for the systolic portion, $\beta_S$ and the diastolic portion 13D, where ($\delta A/A$) is the change in area over original area at a pulse pressure of P. $\Delta P$ is systolic minus diastolic pressure, GR is the radial secant shear modulus, $\beta_S$ is a power law coefficient for the systolic, i.e. loading (pressurizing) path, a is the inner wall radius, b is the outer wall radius, and $\beta_D$ is a power law coefficient for the diastolic, i.e. depressurizing (unloading) path. For a $\beta_S$=1, the model is linear elastic, for $\beta<1$, the model softens with increasing pressure, and for $\beta_s>1$, the model stiffens with increasing pressure. The simple anelastic power law model has been used to model arteries, both large and small, the aorta, the arterioles and veins. The small and large arteries have similar power law coefficients of $\beta_s<1$ at rest and $\beta_s>1$ when vasodilated, while the aorta is much different having $\beta_S>1$, as do the arterioles.

The normalized arterial pulse pressure (P) versus normalized arterial pulse volume, being the change in area over original area, i.e. ($\delta A/A$) of the three component thick wall anelastic power law model fitted to the normotensive subjects data, is shown in FIG. 5. The rise (pressurizing) portion of the pulse pressure versus pulse volume for the power law model fitted to the measured data, is shown as 25, with a power law model value of $\beta_S$=0.8, and the purely fall (depressurizing) portion is denoted as 26, with a power law model value of $\beta_D$=0.4. As the arterial blood vessels are anelastic, they experience small load/unload cycles as the various pulse waves of the waveform arrive, as denoted by 21. The anelasticity of the model is given by the Quality factor, Q, which is the inverse of the energy lost divided by the total energy over a complete load/unload cycle. The Quality factor is related to the power law loading and unloading coefficients as given by equation (2).

$$Q^{-1} = \frac{1 - \beta_P \beta_D}{1 + 2\beta_D + \beta_P \beta_D} \qquad (2)$$

The area between the load/unload paths 25 and 26 is the energy lost during a complete load/unload cycle. For a $\beta$ of 1 the model is linear elastic and thus Q tends to infinity, i.e. zero energy loss. The Quality factor, Q, for the fitted model shown in FIG. 5 is equal to 3.1, being considered the expected value of healthy arterial vascular blood vessels in vivo.

The blood vessels are composed of collagen (endothelium), elastin, smooth muscles and connective tissue. The arteries and veins differ significantly in their anelasticity, due to their significant different functions and applied loads. In the arteries, the collagen, elastin and smooth muscle have values of shear modulus in descending order of ~$10^7$ to $10^6$, and $10^5$ and $10^4$ $Nm^{-2}$, respectively. The arterial elastic lamellae and smooth muscle cells are wrapped by a network of collagenous fibrils. Most of the collagen fibers are orientated circumferentially, but some are orientated obliquely and others longitudinally. Elastin and collagen fibers contribute to the artery's elasticity. In humans, the number of elastic lamella is related to the anatomic location of the artery. Muscular arteries have only one internal and external elastic lamina, while in the aorta there are some 60-90 elastic lamina. The number of elastic lamina decreases gradually towards the periphery of the arterial system. Arterial wall viscosity plays a major role in regulating the mechanical behavior of muscular arteries to their applied loads. The smooth muscle component of the artery wall is considered an important element of the artery that contributes to its viscosity. All components of the artery wall may contribute to its viscosity, but the smooth muscle is the only component to respond to physiological stimulus. Furthermore, these components are influenced both by physiological and pathological changes in the mucopolysaccharide, in which they are embedded. The model could be made more complex with differing layers in the blood vessel wall, anisotropic properties, and also include time dependent effects. However, with that complexity the unique quantification to define the model parameters from non-invasive in vivo measurements becomes unwieldy, so a simple model that contains the essential behavior of the blood vessels' anelastic compliance is preferred. Therefore, the three component model described here is considered a suitable choice; however, the method is not limited to this model's simplicity nor limited to a three component anelastic model, as a fourth component can be added to account for quantifying the effects of arterial vessels' axial tethering in vivo.

FIG. 6 shows the normalized arterial pulse pressure (P) versus the normalized arterial pulse volume, being change in area over original area ($\delta A/A$) for the twenty (20) hypertensive subjects, denoted as 27, constructed from the time shifted PPW and the waveform PVW, denoted earlier as 6 and 7 respectively. The rise (pressurizing) portion of the pulse pressure versus pulse volume is shown as 28, and the fall (depressurizing) portion is denoted as 29. As the arterial blood vessels are anelastic, they experience small load/unload cycles as the various pulse waves of the waveform arrive, as denoted by 30. The three (3) component thick wall anelastic power law model denoted as 22, with inner wall radius 23 and outer wall radius 24, is fitted to the normalized arterial pulse pressure (P) versus normalized arterial pulse volume, being the change in area over original area, i.e. ($\delta A/A$) for the twenty (20) hypertensive subjects. The rise (pressurizing) portion of the pulse pressure versus pulse volume for the power law model fitted to the measured data, is shown as 31, with a power law model value of $\beta_P$=0.5, and the purely fall (depressurizing) portion is denoted as 32, with a power law model value of $\beta_D$=0.4. The Quality factor, Q, for the fitted model shown as 27 in FIG. 6 is Q=2.5, which translates to a 40% energy loss over a complete load/unload cycle, is considered representative of unhealthy arterial vascular blood vessels.

FIG. 7 shows the averaged pulse radial arterial change in area over original area versus radial artery pulse pressure for twenty two (22) normotensive subjects (ranging from 25 to 64 years, mean±SD, 44±11 years) and twenty five (25) hypertensive subjects (ranging from 28 to 72 years, 48±12 years), as detailed in Laurent et al. (1994). The normotensive subjects had blood pressures of 128±21/71±13 mmHg, and the hypertensive subjects had blood pressures of 165±25/96±24 mmHg. The anelastic model fitted data are shown in FIG. 7 as 33, with the pressurizing path of the normotensive subjects being denoted as 34, and the depressurizing path as 35. The pressurizing path for the hypertensive subjects is denoted as 36 and the depressurizing path as 37. The hypertensive subjects all had significant hypertrophy of the radial artery. Comparing the two groups at their respective mean arterial pressures, both groups had similar internal diameters, (internal diastolic diameter 2.53±0.32 and 2.50±0.56 mm), but significantly different intima-media thickness (0.40±0.06 mm and 0.28±0.05 mm, P<0.001) for the hypertensive and normotensive subjects, respectively. Thus, the hypertrophy of the hypertensive group was 43%, being the percentage of growth of the intima-media thickness of the hypertensive group compared to the normotensive group. The anelastic model computed secant shear modulus (GR) values of 510 kPa and 410 kPa for the normotensive and hypertensive subjects respectively, and even though the shear modulus was less in the hypertensive group, the significant hypertrophy thus yielded the same circumferential strain at the inner artery wall at their respective systolic pressures for both groups; highlighting that hypertrophy growth is a means of combating loss of tone, i.e. decreasing values of $\beta_S$ of the hypertensive subjects compared to the normotensive subjects.

FIG. 8 shows the averaged normalized one heart cycle time history for a subset of twenty (20) of the forty (40) normotensive subjects following sublingual administration of 500 μg of glyceryl trinitrate (NTG). The peripheral pulse optical plethysmograph waveform (PVW), denoted as 7, recorded from an optical plethysmograph sensor positioned over a finger, the time history of the constructed first time derivative of the PVW being the dPVW, denoted as 8, and the averaged normalized time history of the peripheral arterial pulse pressure waveform (PPW) recorded over the radial artery by applanation tonometry by a piezo-resistive cantilever transducer, denoted as 6, are shown. The waveforms were recorded 3 minutes after the NTG was administered, which is when the effects of the NTG are at a maximum. The zero ordinate of the constructed waveform dPVW is shown as 10. The first pulse wave peak is denoted as 11. The rise and fall time intervals of the first pulse wave are given by the difference in the time abscissa of points denoted as 12, 13 and 14. With the points, being the intersection of the zero ordinate 10 and the constructed waveform dPVW, point 12 being the start of the rise of the first pulse wave, point 13 being the maximum of the first pulse wave, and point 14 being the end of the fall of the first pulse wave. The ratio of the fall time to the rise time of the first pulse wave for the normotensive subjects as determined from points 12, 13 and 14 is 1.8, which is the same as the forty (40) normotensive subjects prior to any NTG being administered. That is, the NTG had no discernable effect on this fall to rise time ratio of the first pulse wave. The second forward pulse wave is shown as 15 on the pulse volume waveform PVW, 7, and is also shown as 16 on the measured pulse pressure waveform, 6. The second forward pulse wave, which causes closure of the aortic valve, is shown as 17 on the waveform dPVW. The second forward pulse wave peak arrival time location is 0.38 seconds, which is virtually the same as the forty (40) normotensive subjects prior to any NTG being administered.

Note the significant differences in the second forward pulse wave in FIG. 8, i.e. with NTG taken effect, compared to that given in FIG. 3 for the subjects prior to any NTG being administered. The second forward pulse wave in FIG. 3 is 0.65 of the maximum pulse volume, and in FIG. 8 it is 0.31, denoted as the ratio of 38 to 39, and in this case being a percentage drop of 48% from the forty (40) normotensive subjects to the twenty (20) subset normotensive subjects following NTG administration. Similarly, the pulse pressure drops significantly, from 0.31 in FIG. 3, prior to NTG being administered, to 0.16, after NTG, as shown in FIG. 8, for the normotensive subjects prior and after NTG being administered. The ratio of the normalized pulse volume drop or rise is a quantitative indicator of the extent of vasodilation or vasocontraction, as also are the changes in $\beta_S$.

FIG. 9 shows the normalized arterial pulse pressure versus normalized arterial pulse volume for the subset of twenty (20) of the forty (40) normotensive subjects, three (3) minutes after NTG administration, denoted as 40, constructed from the waveforms PPW and PVW, denoted earlier as 6 and 7, respectively. The rise (pressurizing) portion of the pulse pressure versus pulse volume is shown as 41, and the fall (depressurizing) portion is denoted as 42. As the arterial blood vessels are anelastic, they experience small load/unload cycles as the various pulse waves of the waveform arrive, as denoted by 43. The three (3) component thick wall anelastic power law model denoted as 22, with inner wall radius 23 and outer wall radius 24, is fitted to the normalized arterial pulse pressure (ΔP) versus normalized arterial pulse volume (ΔV/V) for the twenty (20) subset of the forty (40) normotensive subjects, subjected to the effects of vasodilation due to NTG being administered. The rise (pressurizing) portion of the pulse pressure versus pulse volume for the power law model fitted to the measured data, is shown as 44, with a power law model value of $\beta_S$=1.25, and the purely fall (depressurizing) portion is denoted as 45, with a power law model value of $\beta_D$=0.4. The Quality factor, Q, for the fitted model shown as 40 in FIG. 9 is Q =4.6, which translates to a 22% energy loss over a complete load/unload cycle, significantly different to the forty (40) normotensive subjects having a Q=3.1. The Quality Factor of Q=4.6 is considered representative of healthy arterial vascular blood vessels, subject to significant vasodilation.

Note the significant difference in the rise (pressurizing) portion of 41 compared to 19, shown in FIG. 5, for the normotensive subjects prior to NTG being administered. The $\beta_S$ value of >1 in FIG. 9, leads to a blood vessel stiffening with pulse pressure, clearly resulting in a significant change in the anelastic response of the arterial vessels to pulse pressure, both loading and unloading, due to vasodilation. In the case of vasodilation, the pulse volume response leads the pulse pressure response up to near the peak pulse volume; whereas, in the normotensive and hypertensive subjects, the pulse pressure leads the pulse volume response with time, during the rise (pressurizing) portion of the arterial vessels. It is the significant changes in the arterial blood vessels anelastic behavior under vasodilation, that result in the observed large drops in normalized pulse volume and normalized pulse pressure during diastolic. The reflected waves are not removed by the vasodilation, but the forward waves including the first pulse wave require a significant larger pulse volume to achieve the same pulse pressure, i.e. when pressurizing up the path 41, compared to pressurizing up the path 19, as is the case for the normotensive subjects. Thus, any forward waves result in much lower induced pulse pressure for the dilated arteries, and their reflected components are also much reduced. In the depressurizing state, a small change in pulse volume results in a significant change in pulse pressure, i.e. following path 42 compared to 20, and thus accounts for the large changes seen in the diastolic phase.

Induced vasocontraction is analogous to a negative pressure applied to the inner wall of the arterial blood vessels, and thus unloads the vessels along the unloading path of the anelastic model. Thus, for a very small contraction pressure, a moderate contraction volume change is achieved, requiring a rise in internal pressure to overcome the vasocontraction. Further increase in pulse pressure follows the loading (pressurizing) path, similar to the hypertensive subjects as denoted by the anelastic model as 31, and then on unloading (depressurizing) the path denoted as 32, as shown in FIG. 5. Significant vasocontraction results in a high Q value, thus giving rise to significant damping of the high frequency shear waves.

The contracted arteries unload (depressurize) along the path denoted as 32, but the arterial pressure remaining, as mentioned earlier to overcome the vasocontraction effect, will only dissipate by arterial windkessel flow, and can be ~20% of the maximum pulse pressure. This impact results in the fall to rise time ratio of the first pulse wave to be <1 for the case of vasocontraction, as the early rise in pulse pressure has no induced pulse volume change, and so the initial rise time of the first pulse wave will be longer than the fall time. Therefore, vasocontraction not only increases the diastolic arterial pressure quite significantly for a small applied contraction pressure, but also increases the pulse pressure, and combined, significantly raises the systolic arterial pressure.

FIG. 10 shows the normalized arterial pulse volume plotted against the normalized arterial pulse pressure 46, for the normotensive group, hypertensive group, and the normotensive subset group subjected to NTG for the pressurizing phase only, being denoted as 47, 48 and 49 respectively. Their respective normalized arterial pulse velocities are shown as denoted by 50, 51 and 52 respectively. Note the significant change in pulse velocity for all three groups as a function of pulse pressure. At 65% of the normalized pulse pressure, all three groups have normalized arterial pulse velocities all virtually the same, at a normalized value of 1.0, as denoted by 53.

FIG. 11 shows the time histories 54 of the waveform PVW 7, measured over the radial artery by the disclosed processing device. The first time derivative dPVW is shown as 8. These waveforms were collected on a mildly hypertensive male of 69 years of age before exercise. After exercise the same waveforms were collected and constructed as denoted by 55 and 56. Note the significant increase in amplitude in the waveform PVW after exercise, comparing 55 to 7, and the reduction in the amplitude of the prime reflective wave, 9 versus 57. Interestingly, the prime reflective wave arrival time, being a two way travel time, are virtually the same, 58 and 59, being 0.23 seconds before exercise and 0.24 seconds after exercise. The pulse wave velocity measured from the subject's brachial artery at the elbow to the radial artery, yielded a pulse wave velocity of 6.9m/sec. The prime reflected wave is assessed to be reflected from the fingertips, back to the upper arm pit, where due to the numerous arteries (axillary, subclavian, etc.) the wave is reflected back down the brachial artery to the radial artery, for a two wave travel path for this subject of 1.6 m for a pulse wave velocity of 6.6 m/sec prior to exercise, and 6.3m/sec after exercise. The pulse pressure experienced by the prime reflected wave, integrated over its travel path using the waveform PPW is 65% of the arterial maximum pulse pressure, and thus explains why there is little to no difference in the arrival time of the prime reflected wave in the before exercise and after exercise conditions, even though there are significant differences in pulse pressure, and the significant dependence of pulse wave velocity on arterial pulse pressure as shown in FIG. 10.

From waveforms PPW and PVW of the mildly hypertensive 69 year old male subject of FIG. 11, the systolic power law coefficient was determined as 0.67, being midway between the normotensive and hypertensive subjects given in FIGS. 5 and 6. Assuming a linear relationship between hypertrophy and the systolic power law coefficient, the a/b ratio of the mildly hypertensive 69 year old male subject is 0.785, from data given in FIG. 7, for a/b=0.81 and 0.75 for the normotensive and hypertensive subjects, respectively.

The tube wave or Stoneley wave as it is generally referred to in geophysics, is a fluid wave travelling in a borehole, and has been extensively studied, originating from the pioneering work of Biot in the 1950s. The conical wake of excited shear waves generated by the Stoneley wave in a slow medium was first observed in the early 1960s. In arterial biomechanics, it appears that the wake of pulse generated high frequency highly dispersive shear waves has been overlooked, even though they are clearly evident in the peripheral arteries, both small and large, in the aorta, and the veins. In optical coherence tomography, the physics is well known and utilized. By focusing the ultrasonic "pushing" beam at a speed greater than the tissue shear wave speed, a wake of excited intense shear waves are generated along a Mach cone creating a plane of intense shear waves propagating in opposite directions. The arterial and venous pulses excite a wake of high frequency shear waves with a Mach angle of 90°, so the shear waves propagate along the vascular vessels as a guided wave. The pulse generated wake of high frequency shear waves gives rise to oscillatory pressure and suction waves acting on the vascular vessel, which have been consistently misinterpreted in the literature in the carotid, brachial and radial as reflected pressure waves. The wake of pulse generated high frequency shear waves also occur in the veins, but at much lower amplitudes than the arteries.

The wake of intense excited shear waves, generated by the traveling pulse, have a particle motion perpendicular to the axial (longitudinal) arterial direction, thus setting up periodic oscillatory waves of pressure and suction, that are highly dispersive. Note that the excited shear wave intensity is much less after exercise compared to at rest. During exercise the vascular smooth muscle relaxes and the radial secant shear modulus ($G_R$) drops significantly, resulting in the radial Bramwell-Hill wave speed being much lower during exercise compared to at rest. The amplitude of the excited shear waves is dependent on the ratio ($C_{BH}/C_L$), i.e. the radial Bramwell-Hill wave speed to the longitudinal shear wave speed, the greater the ratio the higher the induced shear wave amplitude. Since the contrast between the radial and longitudinal wave speeds during exercise compared to at rest is less, then the pulse excited wake of shear waves has a lower amplitude during exercise compared to at rest.

The formulation of the pulse wave velocity (PWV) in the arteries, follows the same procedure as outlined in the geophysics literature, with the p-wave wave speed of the fluid in the geophysics case being substituted by the radial Bramwell-Hill wave speed. The artery longitudinal shear modulus, incorporating the arterial longitudinal wave shear modulus plus arterial embedment and tethering, is analogous to steel casing and the host rock formation as detailed earlier in the geophysics literature of the 1960s. Assuming the same density for blood and tissue, then the arterial PWV is given by equation (3) as detailed below, $$c_P = \frac{c_{BH} c_L}{\sqrt{c_{BH}^2 + c_L^2}} \qquad (3)$$

where $C_P$ is the arterial pulse wave speed, being the PWV. $C_{BH}$ is the arterial radial Bramwell-Hill wave speed, being the Frank/Bramwell-Hill Equation, given by $$c_{BH}^2 = \frac{A}{\rho} \frac{\delta P}{\delta A},$$

where $\rho C^2_{BH} = G_{BH}$ with $G_{BH}$ being the Bramwell-Hill modulus. $C_L$ is the arterial longitudinal shear wave speed, which includes the effects of artery embedment and tethering, with $\rho C^2_L = G_L$ the arterial longitudinal shear modulus. The PWV is significantly different from the $C_{BH}$, especially in the peripheral arteries, due to the artery longitudinal shear wave speed $C_L$ being much lower than radial $C_{BH}$ wave speed.

Knowing the subject's two PWVs ($C_p$), at rest and after exercise, then $C_L$ and the two secant $C_{BH}$ wave speeds (at rest and after exercise) can be determined from equation (3).

By measuring a subject's left radial waveforms PPW and PVW, both at rest and after exercise, the secant anelastic properties of the artery can be determined. The prime reflective pressure wave in the left arm is reflected from the fingertips and back from under the armpit. From the subject's left arm length, and the two wave travel times for at rest and after exercise, CP at rest and after exercise can be found. This reflective wave travels along the arm from systole to below mid-diastole. The $C_{BH}$ wave speed of the prime reflected pressure wave is the tangential $C_{BH}$ velocity at mid-diastole. The diastolic portion is subject insensitive and the tangential $C_{BH}$ at mid-diastole is almost exactly the same as the systolic secant $C_{BH}$ for all subjects.

From the ratio of the PPWs and the PVWs at systole, two equations derived from (3) for at rest and after exercise, can be solved for the respective δA/As at systole and the secant $C_L$ at systole, provided one of the ΔPs, either at rest or after exercise is known. Due to the significant change in pulse pressure following exercise any delay in measuring ΔP will result in significant error, thus the at rest ΔP is preferred to be used. As given in FIG. 11 a mildly hypertensive 69 yr old male had CP of 6.6 m/s and 6.3 m/s at rest and after exercise, and PPW and PVW ratios of at rest to after exercise of 0.61 and 0.49. Solving the two equations, yields radial secant Bramwell-Hill wave speeds ($C_{BH}$) of 10.5 m/s and 9.4 m/s for at rest and after exercise, and a $C_L$ of 8.5 m/s. The subject's at rest ΔP was 42 mmHg, yielding a δA/A at systole of 0.049 for the at rest state, and a δA/A at systole of 0.1 for after exercise.

Assuming a density of blood and tissue of 1040 Kgm/m$^3$, the subject's left arm longitudinal secant shear modulus GL is 75 kPa, compared to the radial secant Bramwell-Hill (GBH) moduli of 115 kPa and 95 kPa, for before and after exercise. That is, the pulse wave is travelling in a "slow" medium, and the pulse generates and excites a wake of high frequency highly dissipative shear waves, that produce oscillatory pressure and suction waves on the vascular vessel, be it an artery or vein. These shear wave induced oscillatory pressure and suction waves have been misidentified in the past as reflective pressure waves, since wave intensity analysis can't discern and differentiate between the pulse exited wake of shear waves from other traveling waves. Relaxation of the vascular smooth muscle during exercise significantly reduced the radial secant modulus GBH by 18%, i.e. from 115 kPa to 95 kPa. For younger healthy subjects, the reduction in the radial secant modulus GBH by smooth muscle relaxation during exercise can be much greater.

The above coupling of the PWV with the arterial longitudinal shear modulus ($G_L$), which includes the effects of artery embedment and tethering, highlights why PWV is a poor indicator of the biomechanical properties of arteries, both small and large. Re-analysis of earlier experimental work has shown that significant systemic changes occur in (HT) subjects, which have earlier been overlooked and have led to conclusions, that the stiffnesses of peripheral arteries increase less or not at all with increasing age or hypertension. As shown here, from a re-analysis of historical data, the peripheral radial artery shows significant changes in its biomechanical properties due to hypertension. The systolic power law coefficient changes from 0.8 (NT) to 0.5 (HT), the radial secant shear modulus drops from NT to HT, hypertrophy is added in HT subjects, and the overall stiffness of the artery is increased in HT subjects.

FIG. 12A depicts the time histories 61 of the waveforms PPW 6, PVW 7, and PUW 62 over a single cardiac cycle measured over the carotid artery by the disclosed processing device. These waveforms were collected on a mildly hypertensive male of 69 years of age at rest, i.e. before exercise, the same subject as given in FIG. 11 for the radial artery. Note that the waveforms PPW and PUW are virtually in-phase during the systolic phase, and only deviate during the diastolic phase. The waveforms PPW and PUW are related to $C_{BH}$ through the momentum jump (shock) condition for the special case when the flow velocity is negligible compared to the wave speed, i.e. δP=ρ$C_{BH}$DδU. The anelastic power law model, equation (1) differentiated with respect to the pulse pressure, yields the tangential systolic velocity CBH, and integrated over the characteristic quantifies the blood velocity as a function of pulse pressure. The wave intensity analysis waveform dPdU calculated from the waveforms PPW and PUW is shown as 63. Positive values of dPdU are forward traveling waves and negative values are backward traveling waves. The zero ordinate of dPdU is shown as 64. Note, there are virtually no backward waves observed in the carotid artery, which is in stark contrast to the radial artery where numerous reflected waves are observed.

The pulse excited wake of high frequency shear waves result in oscillatory pressure and suction waves, as shown by 65 and 66. The period of these shear waves is given by the time abscissa values of 65 and 66 and for this subject has a period of ~0.18 secs compared to his left radial artery of 0.16 secs. The shear wave period is greater in the carotid compared to the radial artery, due to the carotid's larger diameter resulting in a slower period of oscillation of the pulse generated wake of high frequency shear waves.

The arterial mechanical behavior described to date, has concentrated on the small peripheral arteries, primarily the radial artery. For example, a 69 year old male mildly hypertensive, age related, with a resting BP of 124/75 mmHg was recorded over the left radial artery both before and after exercise as shown in FIG. 11. The anelastic model power law coefficients were $β_S$=0.67 and a$β_D$=0.4 at rest, and $β_S$=1.1 and a $β_D$=0.5 after exercise, for the left radial artery. Similar measurements were conducted on the subject's right carotid artery, with the at rest waveforms shown in FIG. 12A for a single cardiac cycle. The carotid anelastic power law coefficients were the same as the subject's radial artery, for both at rest and after exercise.

The suction wave due to the closure of the aortic valve is shown as 67. Note it is a forward traveling wave, positive dPdU, and being a suction wave results in decreasing the magnitude of both the pulse pressure PPW and pulse velocity PUW. Integrating the waveform PUW over the time abscissa values 68 to 69, yields the normalized ejected volume of the left ventricle 70. Integrating the change in the waveform PUW from a linear decline from systole to end of diastole over the time abscissa values 69 to 71 (0.063 secs) yields the normalized closure volume 72 of the aortic valve. The ratio of these two normalized volumes (70/72) for this subject is 37.4 for the cardiac cycle shown. That is the heart's ejected left ventricle volume is 37.4 times the closure volume of the aortic valve.

The aortic valve is shown in the open position 73 (FIG. 12C) and the closed position 74 (FIG. 12D). The cross-sectional area of the aortic valve is typically ~2 cm$^2$/m$^2$ of a subject's body surface area (BSA). For this subject's weight and height, his BSA=2 m$^2$, for an aortic valve total cross-sectional area of 4 cm$^2$. The open cross-sectional area of a normal aortic valve of this size is 2.6 cm$^2$, for a closure volume (fully open to fully closed) of 2.35 cm$^3$. The stroke volume of this subject over the cardiac cycle shown in FIG. 12A is 37.4 times 2.35 cm$^3$ being 88 mL. The heart rate is determined from the difference in the time abscissa values of 68 to 75, yielding the subject's heartbeat period for this cardiac cycle of 0.93 secs, i.e. a heart rate of 65 bpm. The cardiac output (CO) is the stroke volume times the heart rate being 5.7 L/min, with the cardiac index (CI=CO/BSA) of 2.9 L/min/m$^2$. The left ventricle ejected volume and the aortic valve closure volume can thus be determined over each cardiac cycle, and their variability displayed as well as their respective time periods. Such variations can quantify valve impulse closure, valve regurgitation, valve compliance and valve conformance for either natural, repaired or artificial heart valves under normal at rest conditions or during differing cardiac stress conditions, such as during exercise stress tests or during simple maneuvers, such as the Valsalva or the modified Müeller maneuver.

The suction wave from the aortic valve closure 67 has been reflected from the aortic bifurcation and arrives as a second forward traveling suction wave shown as 76 at a time abscissa value 77. The difference in the time abscissa values 77 and 69 (0.213 secs), is the time for the aortic valve closure wave to travel from the aortic valve down to the aortic bifurcation, be reflected back, and travel upwards to the carotid artery; minus the time for the actual aortic valve closure wave to travel from the aortic valve to the carotid artery. From the anelastic power law model of the aorta, early to mid-diastole, for normotensive and hypertensive subjects, the downward traveling wave has a tangential wave speed of twice the upward traveling wave's tangential wave speed, due to the differing pressures experienced by the respective upwards and downwards traveling waves. Knowing the distance from the suprasternal notch to the aortic bifurcation, 46 cm for this subject, enables the PWV to be determined for this path length. From the anelastic power law model, the aortic valve closure wave in the carotid travels at twice the wave speed of the reflected aortic valve closure wave in the carotid artery. The distance from the suprasternal notch to the carotid measuring point is 9 cm, and two measurement points in the carotid would yield the carotid PWV. The subject's aortic PWV is 6.7 m/s, which is equivalent to the secant aorta PWV for the applied pulse pressure (systole minus diastole). This path length entails the most important artery in the body, the aorta, and thus its PWV is of significant clinical interest, and a simple direct measurement of its PWV is extremely useful. If the integral of the change of the PUW waveform 62 of the reflected aortic closure wave 76 from a linear decline from systole to end of diastole is calculated over the time abscissa values 77 to 78 (0.069secs), the reflected normalized aortic valve closure volume 79 is determined. If there are no earlier reflected waves from the aortic valve closure wave, then the normalized volume 79 will be the same as the normalized volume 72. The Q (Quality factor) of this subject's aorta (from the descending aorta to the aorta bifurcation) is the inverse of 1.0 minus the ratio of the time abscissa values (69–71)/(77–78), i.e. 0.063/0.069 for an aorta Quality factor of 11. Any abnormalities (stiffening, plaque buildup, arteriosclerosis, aneurysm or dissection) in the ascending aorta will be apparent from changes in the PPW and PUW during systole and aortic valve closure. Similarly, abnormalities in the descending, thoracic or abdominal aorta will give rise to additional earlier reflected waves before the arrival of the bifurcation reflected aortic valve closure wave, and changes in the PPW and PUW waveforms in the reflected aortic valve closure wave. Location of these abnormalities can be determined from the arrival times of such additional reflected waves. The time abscissa points 68, 69, 71, 75, 77 and 78 correspond to the zero ordinate of the waveform dPdU and the change in slope of the waveform PUW.

The disclosed devices and methods are useful in determining the health status of a subject, more specifically the cardiovascular health status of a subject. In vivo quantification of anelastic changes in arterial blood vessels is essential in diagnosing the issues relating to aging and disease, and determining the impact of medication on changes to the peripheral arterial blood vessels' anelastic properties and their hypertrophy. Arterial hypertrophy refers to the abnormal enlargement or thickening of the walls of arterial blood vessels. This leads to a narrowing of the vascular lumen. Prolonged hypertrophy without intervention can lead to reduced blood supply to the heart, irregular heartbeat, and alterations in blood pressure. The disclosed devices and methods can be used to determine the hypertrophic status of a subject.

Hypertension is often cited as an early cause of hypertrophy. The hypertensive state of a subject can be correlated to age, and as such are related to the effects of aging, or whether the hypertensive state is being accelerated due to the impacts of disease, life style or medication on the respective subject, can be assessed.

Rapid decline in blood pressure or stroke volume can warn of low blood volume (hypovolemia), hypotension perfusion and the imminent risk of the subject entering shock conditions. The disclosed device and methods of use thereof can be used to constantly monitor a subject diagnosed with or suspected of having pneumonia, cardiac disorders, sepsis, asthma, obstructive sleep apnea, hypopnea, anesthesia, pain, or narcotic use. Low stroke volume can indicate onset of endothelium dysfunction (capillary leak syndrome), myocardial dysfunction, hypotension perfusion, respiratory distress or hypoventilation in the subject. In one embodiment, the disclosed devices and methods can be used to monitor mechanical anelastic in vivo properties of the arterial blood vessels, blood pressures, stroke volume, cardiac output, and vascular tone of the subject in real-time in order to alert a physician or caretaker to sudden changes in the subject's health status.

The calculated changes in the arterial blood vessel hemodynamic and anelastic properties can be used to quantify the extent of vasodilation, vasocontraction, loss of stroke volume, induced hypertension/hypotension and possible onset of cardiogenic shock. The determination of the anelastic blood vessel properties provides a direct measure of whether exercise or medication induced vasodilation is sufficient in improving the tone of the subject's peripheral artery blood vessels, and thus reverse or slow the rate of change of the subject's hypertensive state.

The disclosed methods can be used to record the subject's hemodynamic properties, arterial blood vessel anelastic properties, and aortic valve function over time. The historical recoding can enable a physician or caretaker to more accurately determine the impact of current procedures, prescribed medication, diet or exercise program, stress, or other lifestyle changes on the subject's cardiovascular state.

The non-invasive, real-time measurements and calculations of the disclosed method can be used to diagnose cardiovascular diseases and disorders. Changes in cardiac output, blood pressure, or intravascular volume status from a predetermined healthy subject baseline can be indicative of disease. Exemplary cardiovascular diseases and disorders include but are not limited to hypertension, hyperlipidemia, coronary heart disease, atherosclerosis, congestive heart failure, peripheral vascular disease, myocardial infarction, myocardial dysfunction, cardiogenic shock, angina, heart failure, aortic stenosis and aortic dissection.

The disclosed methods can also be used to monitor a subject's response to a treatment for cardiovascular disease. In such an embodiment, measurements are calculated before the subject is administered the treatment to establish a baseline for that subject. Measurements are then calculated throughout treatment. In one embodiment, an unchanged measurement can indicate that the physician should change the treatment type or the amount of treatment that is being administered. Alternatively, if the subject's measurements change to the healthy subject baseline levels, the treatment could be discontinued or tapered down.

Exemplary treatments for cardiovascular diseases and conditions include but are not limited to ACE inhibitors, such as Lisinopril, and benazepril; diuretics, such as hydrochlorothiazide, triamterene, chlorothiazide, and chlorthalidone; beta blockers, such as atenolol, metoprolol, nadalol, labetalol, bisoprolol, and carvedilol; antihypertensive drugs such as losartan and valsartan; calcium channel blockers, such as amlodipine and nifedipine; vasodilators, such as hydralazine; hyperlipidemia medications such as atorvastatin, fluvastatin, lovastatin, pitavastatin, pravastatin, rosuvastatin, and simvastatin; thrombolytic agents such as anistreplase, reteplase, streptokinase, and kabikinase; antiplatelet drugs such as aspirin, clopidogrel, prasugrel, ticagrelor, ticlopidine, dipyridamole, cilostazol, abciximab, eptifibatide, and tirofiban; nitrates; anticoagulants; such as heparin, warfarin, rivaroxaban, dabigatran, apixaban, adoxaban, enoxaparin, and fondaparinux.

In one embodiment, the disclosed methods can indicate that the subject is entering a stage of change in aortic valve closure volume, closure time, or valve regurgitation, that may indicate a possible onset of myocardial dysfunction.

The disclosed methods can also indicate that the subject is entering a stage of change in aorta PWV due to a possibly lower mean blood pressure, acute decline of recirculating blood volume that may indicate a possible onset of cardiogenic shock or myocardial dysfunction or an elevated risk of an aortic aneurysm or dissection.

Changes in aortic function or aortic valve function determined by the disclosed methods and devices can be indicative of aortic valve disease. Aortic valve disease is a condition in which the valve between the left ventricle and the aorta does not function properly. Aortic valve disease may be a condition present at birth, or it may result from other causes.

Aortic valve stenosis is a type of aortic valve disease in which the cusps of the aortic valve become thickened or stiff. In other cases, the cusps may fuse together. Consequently the aortic valve opening is narrowed, thus reducing or blocking blood flow from the heart into the aorta and into circulation. Aortic valve regurgitation occurs when the aortic valve does not close properly, causing blood to flow backward into the left ventricle. Aortic valve regurgitation is also called aortic insufficiency or aortic incompetence.

Aortic valve diseases cannot be treated with medication. The symptoms associated with aortic valve diseases are treated by lifestyle change and medications. Extreme cases of aortic valve disease are treated surgically through the repair or total replacement of the dysfunctional valve.

Finally, it will be understood that the preferred embodiment has been disclosed by way of example, and that other modifications may occur to those skilled in the art without departing from the scope and spirit of the appended claims.

REFERENCES CITED

OTHER PUBLICATIONS

Millasseau S. C., Guigui F. G., Kelly R. P., Prasad K., Cockcroft J. R., Ritter J. M. and Chowienczyk P. J. (2000) Noninvasive Assessment of the Digital Volume Pulse: Comparison with the Peripheral Pressure Pulse, Hypertension 2000;36;952-956. Laurent S., Girerd X., Mourad J., Lacolley P., Beck L., Boutouyrie P., Mignot J. and Safar M. (1994) Elastic Modulus of the Radial Artery Wall Material is not increased in Subjects with essential Hypertension, Arteriosclerosis and Thrombosis, Vol 14, No 7.

What is claimed is:

1. A method of quantifying the aortic valve conformance and compliance in a subject in near real time, the method comprising the steps of:
   a. non-invasively obtaining the pulse arterial pressure waveform (PPW), the pulse arterial volume waveform (PVW) and the pulse arterial velocity waveform (PUW) from the carotid artery in a subject;
   b. constructing a waveform dPdU from the waveforms PPW and PUW;
   c. calculating the aortic ejection volume by integrating the waveform PUW over the time abscissa of the waveform dPdU, wherein the first time abscissa is the zero ordinate before the first peak and the second abscissa is the zero ordinate before the suction wave peak;
   d. calculating the aortic valve closure volume by integrating the waveform PUW over the time abscissa of the waveform dPdU, wherein the first time abscissa is the zero ordinate before the suction wave peak, and the second time abscissa is the zero ordinate after the suction wave peak;
   e. calculating stroke volume, heart rate, and cardiac output for the subject using the aortic valve ejection and closure volumes; and
   f. displaying the aortic valve conformance and compliance of the subject.

2. The method of claim 1, wherein the PPW, PVW and, PUW are non-invasively obtained by placing a device comprising a pulse optical plethysmograph sensor, a force sensor, and a velocity sensor over the artery.

3. The method of claim 2, wherein the pulse optical plethysmograph sensor is an infra-red optical plethysmograph sensor, visible light optical plethysmograph sensor or pulse oximetry sensor.

4. The method of claim 2, wherein the force sensor is of the resistive, strain gage, piezoelectric, capacitance or mems type.

5. The method of claim 2, wherein the velocity sensor is of the Hall, ultrasound doppler or mems type, wherein the Hall sensor has an applied magnetic field from a permanent magnet or an electrical activated electromagnet.

6. The method of claim 2, wherein the device is held in place by a neckstrap that applies pressure to the artery in an amount effective to act as a tonometer.

7. The method of claim 6, wherein the applied pressure is from about 10 mmHg to about 50 mmHg.

8. The method of claim 1, further comprising determining the quality factor of the aorta, wherein the quality factor of the aortic is determined by calculating the inverse of 1.0 minus the ratio of the time interval of the aortic closure wave divided by the time interval of the reflected aortic closure wave, wherein the time intervals are the time difference of the time abscissa of the waveform dPdU from the zero ordinate before to the zero ordinate after each of the respective forward traveling suction waves.

9. A method of quantifying the aortic valve conformance and compliance in a subject in near real time, the method comprising the steps of:
   a. placing a device comprising a pulse optical plethysmograph sensor, a force sensor and a velocity sensor over a subject's carotid artery at an applied pressure;
   b. obtaining the pulse arterial pressure waveform (PPW), the pulse arterial volume waveform (PVW) and the pulse arterial velocity waveform (PUW) from the sensors;
   c. constructing a waveform dPdU from the waveforms PPW and PUW;
   d. calculating the aortic ejection volume by integrating the waveform PUW over the time abscissa of the waveform dPdU, wherein the first time abscissa is the zero ordinate before the first peak and the second abscissa is the zero ordinate before the suction wave peak;
   e. calculating the aortic valve closure volume by integrating the waveform PUW over the time abscissa of the waveform dPdU, wherein the first time abscissa is the zero ordinate before the suction wave peak, and the second time abscissa is the zero ordinate after the suction wave peak;
   f. calculating stroke volume, heart rate, and cardiac output for the subject using the aortic valve ejection and closure volumes; and
   g. displaying the aortic valve conformance and compliance of the subject.

10. The method of claim 9, wherein the velocity sensor is of the Hall, ultrasound doppler or mems type, wherein the Hall sensor has an applied magnetic field from a permanent magnet or an electrical activated electromagnet.

11. The method of claim 9, wherein the display includes an alert message or signal generated at critical states of the subject's stroke volume, change in aortic valve closure volume, aortic valve conformance, cardiac output, heart rate, vasodilation/vasocontraction and hypertensive state.

12. The method of claim 9, wherein the stroke volume, change in aortic valve closure volume, aortic valve conformance, cardiac output, heart rate, vasodilation/vasocontraction and hypertensive state of the subject are continuously displayed.

13. A method of diagnosing and treating aortic valve diseases and disorders in a subject in need thereof, comprising:
   a. non-invasively obtaining the pulse arterial pressure waveform (PPW), the pulse arterial volume waveform (PVW) and the pulse arterial velocity waveform (PUW) from the carotid artery in a subject;
   b. constructing a waveform dPdU from the waveforms PPW and PUW;
   c. calculating the aortic ejection volume by integrating the waveform PUW over the time abscissa of the waveform dPdU, wherein the first time abscissa is the zero ordinate before the first peak and the second abscissa is the zero ordinate before the suction wave peak;
   d. calculating the aortic valve closure volume by integrating the waveform PUW over the time abscissa of the waveform dPdU, wherein the first time abscissa is the zero ordinate before the suction wave peak, and the second time abscissa is the zero ordinate after the suction wave peak;
   e. calculating stroke volume, heart rate, and cardiac output for the subject using the aortic valve ejection and closure volumes;
   f. diagnosing the subject with aortic valve dysfunction if the aortic valve ejection volume, aortic valve closure volume, stroke volume, cardiac output, or a combination thereof deviate from a predetermined healthy baseline; and
   g. administering a treatment to the subject of a type and amount effective to reduce the symptoms of aortic valve dysfunction.

14. The method of claim 13, wherein the PPW, PVW and, PUW are non-invasively obtained by placing a device comprising a pulse optical plethysmograph sensor, a force sensor, and a velocity sensor over the artery.

15. The method of claim 14, wherein the pulse optical plethysmograph sensor is an infra-red optical plethysmograph sensor, visible light optical plethysmograph sensor or pulse oximetry sensor.

16. The method of claim 14, wherein the force sensor is of the resistive, strain gage, piezoelectric, capacitance or mems type.

17. The method of claim 14, wherein the velocity sensor is of the Hall, ultrasound doppler or mems type, wherein the Hall sensor has an applied magnetic field from a permanent magnet or an electrical activated electromagnet.

18. The method of claim 14, wherein the device is held in place by a neckstrap that applies pressure to the artery in an amount effective to act as a tonometer.

19. The method of claim 13, further comprising repeating steps (a)-(f) after administration of the treatment.

20. The method of claim 13, wherein the subject has aortic valve stenosis or aortic valve regurgitation.

21. The method of claim 13, wherein the stroke volume is determined by the ratio of the integration of the waveform PUW over the systolic phase, divided by the integration of the waveform PUW over the aortic valve closure time.

22. The method of claim 13, further comprising displaying an indication that the subject is entering a stage of change in aortic valve closure volume, closure time, or valve regurgitation, that may indicate a possible onset of myocardial dysfunction.

23. The method of claim 13, further comprising determined the PWV across the subject's aorta, wherein the PWV across the subject's aorta is determined by calculating the time arrival difference of the actual aortic valve closure wave to the reflected aortic valve closure wave and difference in distance travelled by the reflected wave to the actual aortic closure wave.

24. The method of claim 13, further comprising displaying an indication that the subject is entering a stage of change in aorta PWV due to a possibly lower mean blood pressure, acute decline of recirculating blood volume, that may indicate a possible onset of cardiogenic shock or myocardial dysfunction or an elevated risk of an aortic aneurysm or dissection.

25. The method of claim 13, further comprising determining the quality factor of the subject's aorta, wherein the Quality factor is determined by calculating the ratio of the time interval of the aortic valve closure wave over the time interval of the reflected aortic valve closure wave, with the aorta Quality factor being equal to the inverse of 1.0 minus this ratio.

26. The method of claim 13, further comprising determining that the aortic valve PWV indicates stiffening, plaque buildup, arteriosclerosis and/or elevated risk of aneurysm.

* * * * *